United States Patent
Oshima et al.

(10) Patent No.: US 10,987,258 B2
(45) Date of Patent: *Apr. 27, 2021

(54) PAD TYPE DISPOSABLE DIAPER

(71) Applicant: DAIO PAPER CORPORATION, Ehime (JP)

(72) Inventors: Aya Oshima, Tochigi (JP); Aya Takahashi, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 355 days.

This patent is subject to a terminal disclaimer.

(21) Appl. No.: 16/076,830

(22) PCT Filed: Feb. 9, 2017

(86) PCT No.: PCT/JP2017/004739
§ 371 (c)(1),
(2) Date: Aug. 9, 2018

(87) PCT Pub. No.: WO2017/138610
PCT Pub. Date: Aug. 17, 2017

(65) Prior Publication Data
US 2019/0046367 A1 Feb. 14, 2019

(30) Foreign Application Priority Data

Feb. 10, 2016 (JP) .............................. JP2016-024184

(51) Int. Cl.
*A61F 13/15* (2006.01)
*A61F 13/533* (2006.01)
(Continued)

(52) U.S. Cl.
CPC ...... *A61F 13/533* (2013.01); *A61F 13/51104* (2013.01); *A61F 13/51121* (2013.01);
(Continued)

(58) Field of Classification Search
CPC .......... A61F 13/51108; A61F 13/51104; A61F 13/513; A61F 13/532; A61F 13/15804
(Continued)

(56) References Cited

U.S. PATENT DOCUMENTS 4,327,730 A * 5/1982 Sorensen .............. A61F 13/512
428/131
4,781,710 A 11/1988 Megison et al.
(Continued)

FOREIGN PATENT DOCUMENTS

CN 1976659 6/2007
EP 2656826 10/2013
(Continued)

OTHER PUBLICATIONS

Chinese Office Action for 201780010394.0 dated Jun. 23, 2020.
(Continued)

*Primary Examiner* — Jacqueline F Stephens
(74) *Attorney, Agent, or Firm* — IPUSA, PLLC

(57) ABSTRACT

An absorbent of a disposable diaper is formed of a lower layer absorbent and an upper layer absorbent, wherein a pair of left and right slits is extended in a front-rear direction region including a crotch portion, wherein the left slit and the right slit are spaced apart in a width direction, wherein a top sheet includes a depressed portion that falls into the slits, and wherein, in at least a region located between the slits in the top sheet, a large number of convex portions is arranged in a zigzag manner while being spaced apart by an interval, and the interval between the adjacent convex portions in the width direction is shorter than each of sizes in the width direction of the convex portions located at the front side and at a rear side of a part of the interval.

7 Claims, 22 Drawing Sheets

(51) Int. Cl.
*A61F 13/534* (2006.01)
*A61F 13/511* (2006.01)
*A61F 13/537* (2006.01)
*A61F 13/51* (2006.01)
*A61F 13/53* (2006.01)

(52) U.S. Cl.
CPC .. *A61F 13/534* (2013.01); *A61F 2013/51026* (2013.01); *A61F 2013/51147* (2013.01); *A61F 2013/530007* (2013.01); *A61F 2013/53445* (2013.01); *A61F 2013/530481* (2013.01); *A61F 2013/53778* (2013.01)

(58) Field of Classification Search
USPC .......................................... 604/378, 379, 380
See application file for complete search history.

(56) References Cited

U.S. PATENT DOCUMENTS

| | | | |
|---|---|---|---|
| 4,846,821 | A | 7/1989 | Lyons et al. |
| 5,846,231 | A | 12/1998 | Fujioka et al. |
| 6,563,013 | B1 * | 5/2003 | Murota ............... A61F 13/4704 604/379 |
| 2002/0065498 | A1 * | 5/2002 | Ohashi ................. A61F 13/536 604/379 |
| 2003/0143376 | A1 | 7/2003 | Toyoshima et al. |
| 2006/0116653 | A1 | 6/2006 | Munakata et al. |
| 2008/0262459 | A1 | 10/2008 | Kamoto et al. |
| 2010/0063470 | A1 | 3/2010 | Suzuki et al. |
| 2012/0220971 | A1 | 8/2012 | Harada et al. |
| 2015/0250659 | A1 | 9/2015 | Tally et al. |
| 2015/0290050 | A1 | 10/2015 | Wada |
| 2017/0014280 | A1 | 1/2017 | Moritani |
| 2017/0135869 | A1 | 5/2017 | Moriya et al. |

FOREIGN PATENT DOCUMENTS

| | | |
|---|---|---|
| JP | 2620305 | 6/1997 |
| JP | H10-314217 | 12/1998 |
| JP | 2003-250836 | 9/2003 |
| JP | 2007-175248 | 7/2007 |
| JP | 2008-520401 | 6/2008 |
| JP | 2012-157380 | 8/2012 |
| JP | 2013-255557 | 12/2013 |
| JP | 2015-039579 | 3/2015 |
| JP | 2015-044046 | 3/2015 |
| JP | 2015-188453 | 11/2015 |
| JP | 2016-013209 | 1/2016 |
| JP | 2016-022282 | 2/2016 |
| WO | 2011/034180 | 3/2011 |
| WO | 2011/142272 | 11/2011 |
| WO | 2014/050310 | 4/2014 |

OTHER PUBLICATIONS

International Search Report for PCT/JP2017/004739 dated May 9, 2017.
Extended European search report for European Patent Application No. 17750331.5 dated Feb. 20, 2019.
International Search Report for PCT/JP2016/075998 dated Dec. 6, 2016.
Office Action dated May 6, 2020 issued to related U.S. Appl. No. 15/757,774.
Final Office Action dated Sep. 29, 2020 issued to related U.S. Appl. No. 15/757,774.

* cited by examiner (a)

(b)

(a)

(b)

(a)

(b)

(a)
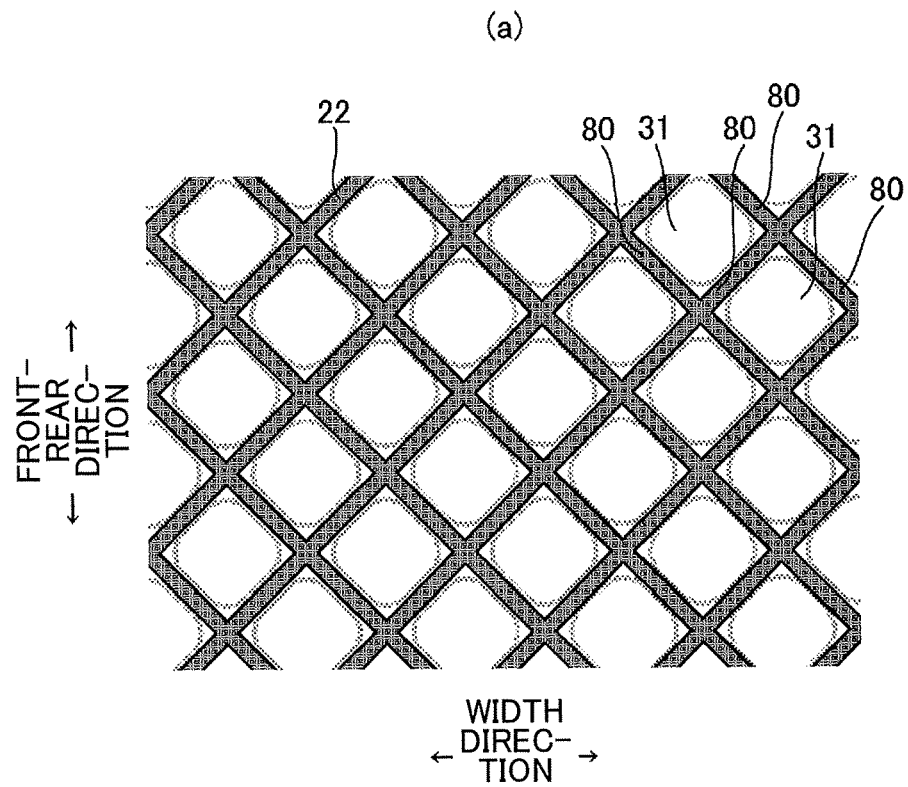
FIG.21
(b)
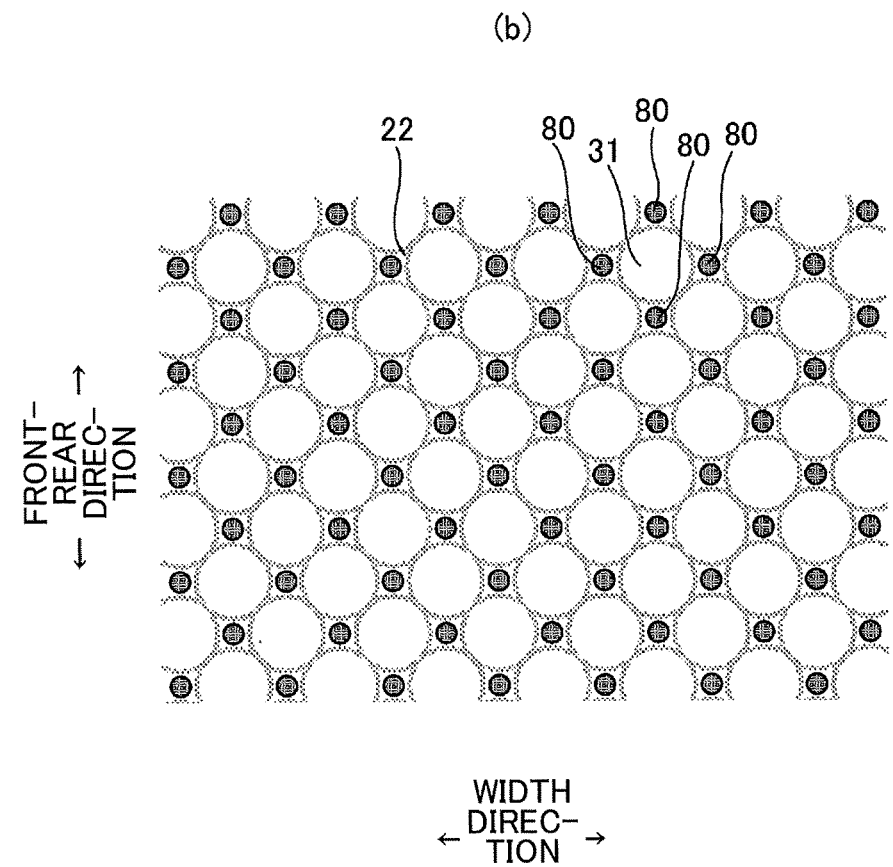

PAD TYPE DISPOSABLE DIAPER

TECHNICAL FIELD

The present invention relates to a pad type disposable diaper with large absorption capacity, that is excellent in a reversion preventing property, and that has excellent crotch fit characteristics.

BACKGROUND ART

One of typical absorption properties required for a disposable diaper is absorbable capacity. Usually, the absorbable capacity is determined depending on a use of a product. For example, a product assumed to be used at night, in particular a nighttime product for an adult, is a product with large absorption capacity, in general. In such a product, in order to reserve an absorbable amount, an absorbent often has a vertical two-layer structure.

As illustrated in FIG. 22, an absorbent of an absorbent product is, in general, formed by mixing and accumulating pulp fibers $23f$ and superabsorbent polymer particles $23p$. Upon absorption by such absorbents 23A and 23B, as illustrated in the absorption state change in the figure, the superabsorbent polymer particles $23p$ located on the surface side tend to absorb and expand earlier, and gel blocking occurs in which liquid permeability toward the lower side is lowered. Accordingly, it becomes difficult for a liquid component, such as urine, to percolate below the absorbents 23A and 23B. When such gel blocking occurs, the state becomes the same as the state in which absorption by the absorbents 23A and 23B is saturated and the absorption capacity decreases. Even if there exists absorption capacity below the absorbents 23A and 23B, the state becomes such that reversion tends to occur. Reversion is a phenomenon in which the urine once absorbed in the absorbents 23A and 23B from the surface of the diaper returns to the surface of the diaper again. If reversion tends to occur, skin is unnecessarily soiled with excretions, and a problem can be caused such that skin problems tend to occur. Needless to say, but in FIG. 22, the sizes of the superabsorbent polymer particles $23p$ are exaggerated, so that a change in a content rate or absorption expansion of the superabsorbent polymer particles $23p$ can be easily seen.

One method of avoiding gel blocking in a product with the vertical two-layer structure of the absorbent is to extend, in the front and rear direction, a slit that passes through, at least, the upper layer absorbent of the absorbent in the thickness direction so as to include the crotch portion. In this case, the diffusibility of the urine in the front and rear direction is enhanced by the slit, and urine can be directly absorbed by the lower layer absorber through the slit. Accordingly, the urine quickly diffuses in the front and rear direction and in the thickness direction of the absorbent to be absorbed, and the revision caused by gel blocking tends not to occur.

Unlike a sanitary napkin or a urine absorbing pad, in a pad type disposable diaper with large absorption capacity, the width of the absorber is wider than the width of the crotch of a wearer, and the end portions in the width direction of the crotch portion face the respective inner thighs of the wearer. Accordingly, a configuration is common such that the middle portion in the width direction faces the crotch. In this case, if a slit is formed along a boundary between the portion facing the inner thigh and the portion facing the crotch, the absorbent can be easily bent at the slit as the boundary, so that the crotch fitting characteristics can be enhanced. Thus, the present inventors have attempted to adopt the arrangement of the pair of slits as the reversion preventing slits in the above-described absorbent with the two-layer structure.

In this case, however, a problem is that a urine discharge position is not above the slit. Accordingly, the amount of urine flowing into the slit decreases, and the reversion preventing effect is also reduced. Namely, in a product in which the absorbent has the vertical two-layer structure, it has been difficult to enhance both the reversion preventing property and the crotch fitting characteristics by providing a slit in the absorbent. Here, in addition to the slits at the sides in the width direction, it can be attempted to add a center slit at the middle portion in the width direction. However, it is not desirable because the absorbable capacity is reduced due to an increase in the area of the slit.

RELATED-ART DOCUMENTS

Patent Document

Patent Document 1: Japanese Patent No. 5669976
Patent Document 2: Japanese Unexamined Patent Publication No. 2013-255557

SUMMARY OF THE INVENTION

Problem to be Solved by the Invention

A main object of the present invention is to provide a pad type disposable diaper that has large absorption capacity, that has a superior reversion preventing property, and that has superior crotch fitting characteristics.

Means to Solve the Problem

The present invention that solves the above-described problem is as follows.

A pad type disposable diaper including a crotch portion, a front portion that extends toward a front side of the crotch portion, a rear portion that extends toward a rear side of the crotch portion, an absorbent provided in a front-rear direction range including the crotch portion, and a top sheet covering a surface side of the absorbent, wherein the absorbent is formed of a lower layer absorbent and an upper layer absorbent formed on a surface side of the lower layer absorbent, wherein a pair of left and right slits that pass through only the upper layer absorbent or the upper layer absorbent and the lower layer absorbent in a thickness direction is extended in a front-rear direction region including the crotch portion, wherein each of the pair of left and right slits has a predetermined width, and the left slit and the right slit are spaced apart in a width direction, wherein the top sheet includes a depressed portion that falls into the slits, and wherein, in at least a region located between the slits in the top sheet, a large number of convex portions protruding toward the surface side is arranged in a zigzag manner while being spaced apart by an interval, and the interval between the adjacent convex portions in the width direction is shorter than each of sizes in the width direction of the convex portions located at the front side and at a rear side of a part of the interval.

(Effects)

If a large number of convex portions protruding toward the surface side are disposed on the top sheet while spaced apart by the interval, a gap between the convex portions becomes a concave portion, so that urine on the top sheet tends to flow along a direction in which the convex portions continue. One of the features of the present invention is that, by using this property, urine is facilitated to flow from a urine discharge position to a slit. Namely, the region located between the slits in the top sheet is located at the urine discharge position or located behind the urine discharge position, which is a location at which more urine is supplied due to a slope toward the crotch portion. Here, if, at least in a region located between the slits, a large number of convex portions is arranged in a zigzag manner while spaced apart by an interval, and if the interval between the adjacent convex portions in the width direction is shorter than the width of each of the convex portions located at the front side and the rear side thereof, the concave portions between the convex portions do not linearly continue in the front-rear direction, and continue in an oblique lattice. Thus, urine supplied to the region located between the slits tends to flow obliquely rearward, compared to the front-rear direction. As a result, when urine flows rearward from the urine discharge position, the urine is facilitated to flow into the slits at both sides in the width direction. Accordingly, by providing the slits on only both sides in the width direction, the crotch fitting characteristics can be made excellent and the reversion preventing property can be made excellent, while suppressing a decrease in the absorbable capacity.

Note that the term slit means a part passing through the absorbent from the surface side to the reverse side. Furthermore, the predetermined width of the slit merely means that it does not include a concave groove or a slit without any gap width (the facing side walls contact each other). The predetermined width does not imply that the width is constant, and, thus, the predetermined width includes a concave groove or a slit in which the width varies, as long as it has a width.

The pad type disposable diaper, wherein a weight ratio of superabsorbent polymer particles with respect to pulp fibers in the upper layer absorbent is greater than a weight ratio of the superabsorbent polymer particles with respect to the pulp fibers in the lower layer absorbent.

(Effects)

In the absorbent according to the present invention, though the liquid component of the excrement is supplied to the upper layer absorbent, a majority of the liquid component of the excrement is directly supplied to the lower absorbent through the slit. Here, if the weight ratio of the superabsorbent polymer particles with respect to the pulp fibers in the lower layer absorbent is less than that of the upper layer absorbent, gel blocking tends not occur in the lower layer absorbent compared to the upper layer absorbent, and the liquid component of the excrement diffuses in a wider range within the lower layer absorbent. At least after saturation of the absorption by the lower absorbent, the liquid component absorbed by the lower layer absorbent is suctioned by the upper layer absorbent to be transferred to the upper layer absorbent, and the liquid component is absorbed and held by the upper layer absorbent. At this time, until at last, the absorption capacity is left at the surface side (skin side) of the absorbent because, in the upper layer absorbent, the weight ratio of the superabsorbent polymer particles with respect to the pulp fibers is high and a larger amount of the liquid component can be absorbed and retained, while the lower layer absorbent preferentially absorbs the liquid component. As a result, the reversion prevention property can further be enhanced.

The pad type disposable diaper, wherein a front end of the slit is separated rearward from a front end of the absorbent, and wherein the region in which the convex portions are arranged extends to the front side of the slit.

(Effects)

When the wearer is in a prone position or in a side lying position, the inclination of the top sheet may fall forward. In such a case, front leakage may occur. Accordingly, as described above, it is proposed to extend the region in which the convex portions are arranged to the front side of the slit, so that the front leakage can be prevented by reducing the diffusibility of the slit at the front side in the front-rear direction, and by promoting the diffusion to the oblique front side.

The pad type disposable, wherein a size in the front-rear direction of the convex portion is from 1.1 mm to 12.0 mm, a size in the width direction of the convex portion is from 2.3 mm to 9.2 mm, and the size in the front-rear direction of the convex portion is 0.5 to 1.3 times the size in the width direction of the convex portion, wherein, in a sequence of the convex portions arranged in the front-rear direction, a distance between centers of the convex portions in the front-rear direction is preferably from 1.9 mm to 20.9 mm, wherein, in a sequence of the convex portions arranged in the width direction, a distance between the centers of the convex portions in the width direction is preferably from 4.0 mm to 16.0 mm, and wherein the distance between the centers of the convex portions in the front-rear direction in the sequence of the convex portions arranged in the front-rear direction is 0.5 to 1.3 times the distance between the centers of the convex portions in the width direction in the sequence of the convex portions arranged in the width direction.

(Effects)

The size and the arrangement interval of the convex portions of the top sheet may preferably be within the range described in the claim.

The pad type disposable diaper, wherein the top sheet is formed of thermoplastic nonwoven fabric, and wherein a low transmission portion, in which fibers are mutually welded in a state in which the fibers are compressed in a thickness direction, is provided between the convex portions in the top sheet.

(Effects)

The low transmission portion is a portion at which the fibers are mutually welded in a state in which the nonwoven fabric of the top sheet is compressed in the thickness direction and the liquid permeability is lowered compared to the surroundings. To this extent, the low transmission portion includes, in addition to a portion in which fiber gaps remain to indicate some permeability, a portion which almost completely becomes a film and that do not transmit liquid at all. If a large number of such low transmission portions are provided between the convex portions in the top sheet, the permeability is restricted, and the diffusibility is enhanced correspondingly. As a result, urine on the top sheet tends to flow into the slit by passing through the gap between the convex portions.

The pad type disposable diaper, wherein a plurality of low transmission portions is formed while spaced apart by a gap.

(Effects)

The low transmission portions may be continuously formed. However, flexibility of the top sheet is lowered. Accordingly, the low transmission portions may preferably be formed while spaced apart by the gap.

The pad type disposable, wherein, while the fibers are mutually welded in the low transmission portion, the low transmission portion is welded to a component at a reverse side.

(Effects)

The low transmission portion of the top sheet may be provided in any form. However, the low transmission portion of the top sheet may preferably be provided also to secure the top sheet to the component at the reverse side.

The pad type disposable, wherein the convex portions are also formed in the depressed portion.

(Effects)

As described above, if the convex portions are formed in the depressed portion, even if the crotch portion is nipped between legs of the wearer and the absorbent shrinks to some extent in the width direction to collapse the slit in the width direction, gaps are maintained around the convex portions and the enhancement in the diffusibility is not easily damaged.

Advantage of the Invention

As described above, according to the present invention, advantages can be obtained such that a pad type disposable diaper is provided that has large absorbable capacity, that is superior in the reversion prevention property, and that is superior in crotch fitting characteristics.

BRIEF DESCRIPTION OF THE DRAWINGS

FIG. 21 is an enlarged plan view of a pattern of a low transmission portion.

MODE FOR CARRYING OUT THE INVENTION

Figure 1:
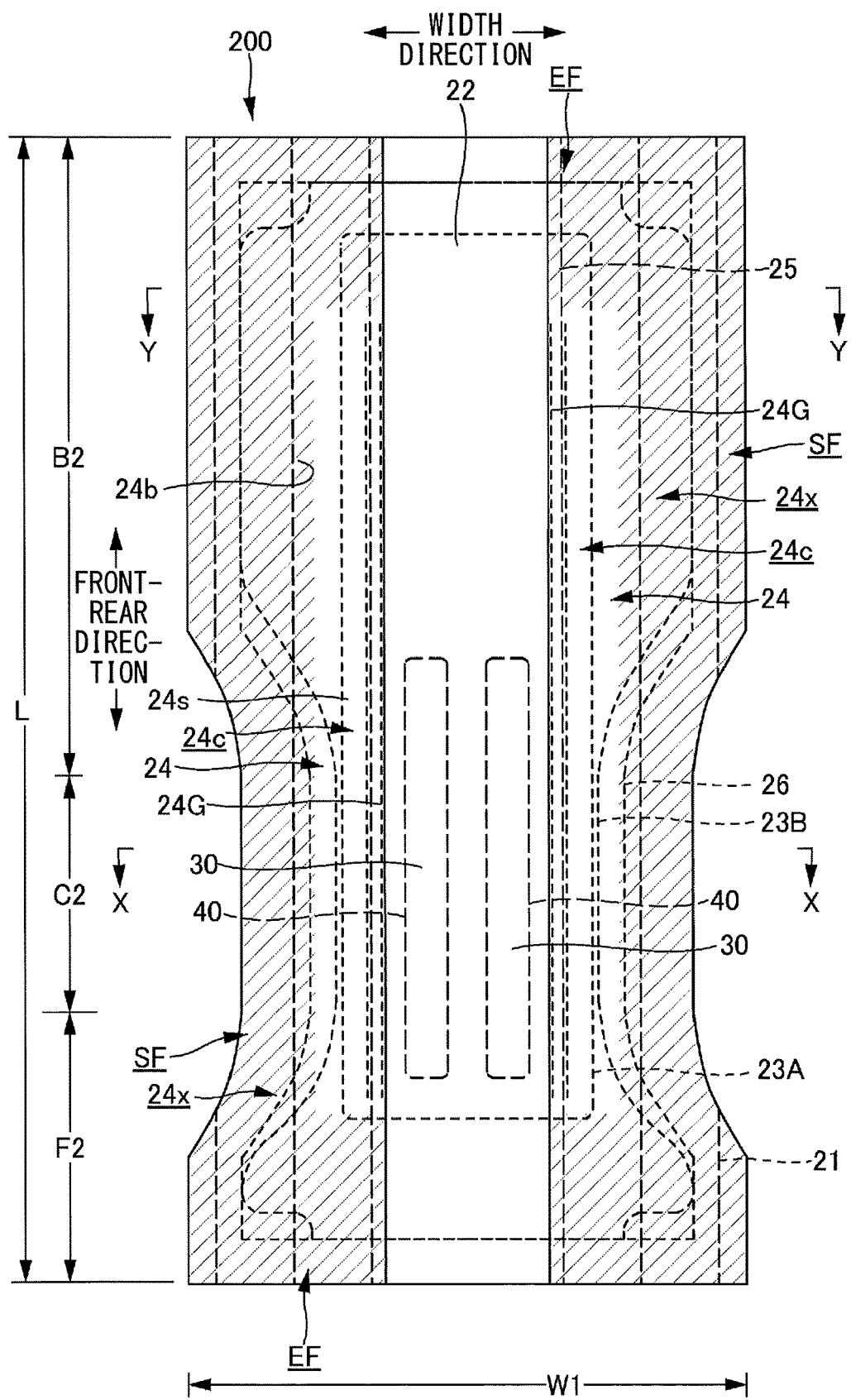
FIG. 1 is a plan view illustrating an inner surface side of a pad type disposable diaper in a developed state.

In the following, an embodiment of the present invention is described in detail by referring to the accompanying drawings. In the terms of the present invention, the "crotch portion" means a portion corresponding to a crotch of a body during use. Depending on a product, the "crotch portion" may be, as depicted, in a range from a center in a front-rear direction of the product or from the vicinity thereof to a predetermined part in a front side, or may be in a predetermined range of the center of the product in the front-rear direction. If there is a narrow constriction at the center of the product in the front-rear direction or at the center of an absorbent in the front-rear direction, the "crotch portion" means a predetermined range in the front-rear direction with a center in the front-rear direction that is a minimum width part of one of the constrictions or both the constrictions. Further, the "front side portion (ventral part)" means a portion in the front side compared to the crotch portion. The "rear side portion (dorsal part)" means a portion in the rear side compared to the crotch portion.

FIG. 1 through FIG. 4 illustrate an example of a pad type disposable diaper 200 according to the present invention. The pad type disposable diaper 200 is provided with a crotch portion C2; and a front portion F2 and a rear portion B2 that extend on front and rear sides of the crotch portion C2. A size of each part can be determined as appropriate. For example, a total length of the product (the length in the front-rear direction) L may be approximately from 350 mm to 700 mm, and a total width W1 may be approximately from 130 mm to 400 mm (however, it is wider than a width of an absorption surface of the diaper). In this case, a length in the front-rear direction of the crotch portion C2 may be approximately from 10 mm to 150 mm, a length in the front-rear direction of the front portion F2 may be approximately from 50 mm to 350 mm, and a length in the front-rear direction of the rear portion B2 may be approximately from 50 mm to 350 mm. Additionally, a width W3 of the crotch portion C2 may be greater than or equal to 150 cm, in particular approximately from 200 cm to 260 cm, for adult use.

The pad type disposable diaper 200 has a basic structure in which absorbents 23A and 23B are interposed between a liquid impermeable sheet 21 and a liquid permeable top sheet 22.

On the reverse side of the absorbents 23A and 23B, the liquid impermeable sheet 21 is provided so as to protrude slightly form fringes of the absorbents 23A and 23B. As the liquid impermeable sheet 21, in addition to a polyethylene film, etc., a sheet with moisture permeability that does not damage a water proof property may be used, from a viewpoint of prevention of stuffiness. As the water proof/moisture permeable sheet, a microporous sheet may be used, which can be obtained, for example, by forming a sheet by melting and mixing an inorganic filler in an olefin resin, such as polyethylene or polypropylene, and, then, by extending the sheet in a uniaxial direction or biaxial directions.

An outer surface of the liquid impermeable sheet 21 is covered with an outer covering sheet 27 formed of nonwoven fabric. The outer covering sheet 27 protrudes outside a fringe of the back sheet 21 by a predetermined protruding width. As the outer covering sheet 27, various types of nonwoven fabric may be used. As a raw material fiber forming the nonwoven fabric, in addition to an olefin type synthetic fiber, such as polyethylene or polypropylene, an polyester type synthetic filer, and an amide type synthetic fiber, a regenerated fiber, such as rayon and cupra, and a natural fiber, such as cotton, may be used. The outer covering sheet 27 may be omitted.

Front sides of the absorbent 23A and 23B are covered with the liquid permeable top sheet 22. In the depicted embodiment, parts of the absorbents 23A and 23B protrude from side edges of the top sheet 22. However, the width of the top sheet 22 may be enlarged so that side edges of the absorbents 23A and 23B do not protrude. As the top sheet 22, porous or non porous nonwoven fabric or a plastic sheet with holes may be used. As a raw material fiber forming the nonwoven fabric, in addition to an olefin type synthetic fiber, such as polyethylene or polypropylene, an polyester type synthetic filer, and an amide type synthetic fiber, a regenerated fiber, such as rayon and cupra, and a natural fiber, such as cotton, may be used.

It is desirable to interpose an intermediate sheet 25 between the top sheet 22 and the absorbents 23A and 23B. The intermediate sheet 25 is provided to prevent reversion of urine absorbed by the absorbents 23A and 23B. It is desirable to use a material with a low water reserving property and high liquid permeability, such as various types of nonwoven fabric and mesh films. Assuming that the front end of the top sheet 22 is 0% and the rear end of the top sheet 22 is 100%, the front end of the intermediate sheet 25 is preferably located within a range from 0% to 11%, and the rear end of the intermediate sheet 25 is preferably located within a range from 92% to 100%. Additionally, a width W4 of the intermediate sheet 25 may preferably be approximately from 50% to 100% of the minimum width W5 of the constriction 23n of the absorbents 23A and 23B, which is described below.

At both end portions in the front-rear direction of the pad type disposable diaper 200, end flap portions EF, in which the absorbents 23A and 23B do not exist, are formed by extending the outer covering sheet 27 and the liquid permeable sheet 22 from the front and rear ends of the absorbents 23A and 23B toward the front and rear sides, and by bonding the outer covering sheet 27 and the liquid permeable sheet 22. At both side portions of the pad type disposable diaper 200, side flap portions SF, in which the absorbents 23A and 23B do not exist, are formed by extending the outer covering sheet 27 from the side ends of the absorbents 23A and 23B toward outside, and by bonding outside portions 24x in the width direction of a gather sheet 24s forming a three-dimensional gather 24 to an inner surface of the portions from the extended portions to the side portions of the top sheet 22, over the entire portions in the front-rear direction. These bonded portions are indicated by oblique lines in FIG. 1 and can be formed by a hot melt adhesive, a heat seal, and an ultrasonic seal. When the outer covering sheet 27 is not provided, the outer surface sides of the side flap portions SF can be formed by extending, instead of the outer covering sheet 27, the liquid impermeable sheet 21 to the side flap portions SF.

As a material of the gather sheet 24s, a plastic sheet or meltblown nonwoven fabric may be used. From the view point of feeling to the skin, nonwoven fabric to which a water repellent treatment using silicon, etc., is applied may preferably be used.

Center side portions 24c of the gather sheet 24s in the width direction extend to the top sheet 22. At the end portions of the center side portions 24c in the width direction, elongated elastic components 24G are fixed in a stretched state along the front-rear direction by a hot melt adhesive, etc. As the elongated elastic component 24G, a material that is usually used can be used, such as a styrene-based rubber, an olefin-based rubber, an urethane-based rubber, an ester-based rubber, a polyurethane, a polyethylene, a polystyrene, a styrenebutadiene, a silicon, a polyester, etc., which are formed in a filamentous shape, a string shape, a beltlike shape, etc.

In each of the gather sheets 24s, the outside portion 24x in the width direction is bonded and fixed to the inner surface of the product (in the depicted embodiment, the front surface of the top sheet 22 and the inner surface of the outer covering sheet 27) over the entire portion in the front-rear direction, the center side portion 24c in the width direction is bonded and fixed to the inner surface of the product (in the depicted embodiment, the front surface of the top sheet 22) at end portions in the front-rear direction, and the center side portion 24c is not fixed to the inner surface of the product (in the depicted embodiment, the front surface of the top sheet 22) between the end portions in the front-rear direction. As illustrated in FIG. 1, this non-fixed portion is a portion to be a leakage prevention wall elastically standing with respect to the inner surface of the product (in the depicted embodiment, the front surface of the top sheet 22). A standing base end 24b of the non-fixed portion is located at the boundary between the outside fixed portion 24x in the width direction and the center side portion 24c in the gather sheet 24x.

Figure 3:
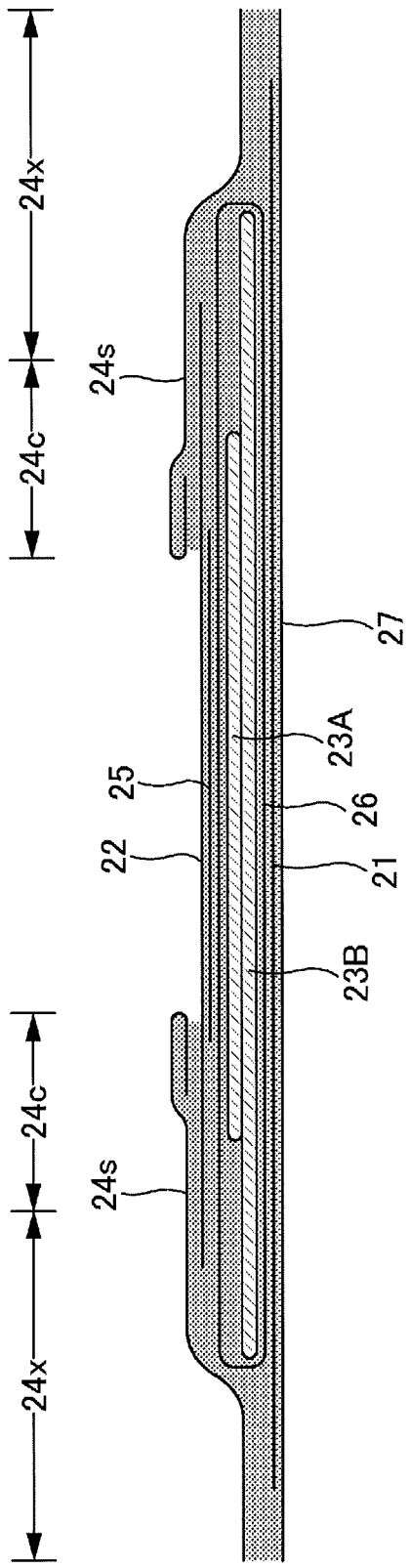
FIG. 3 is a cross-sectional view along Y-Y line of FIG. 1.
Figure 4:
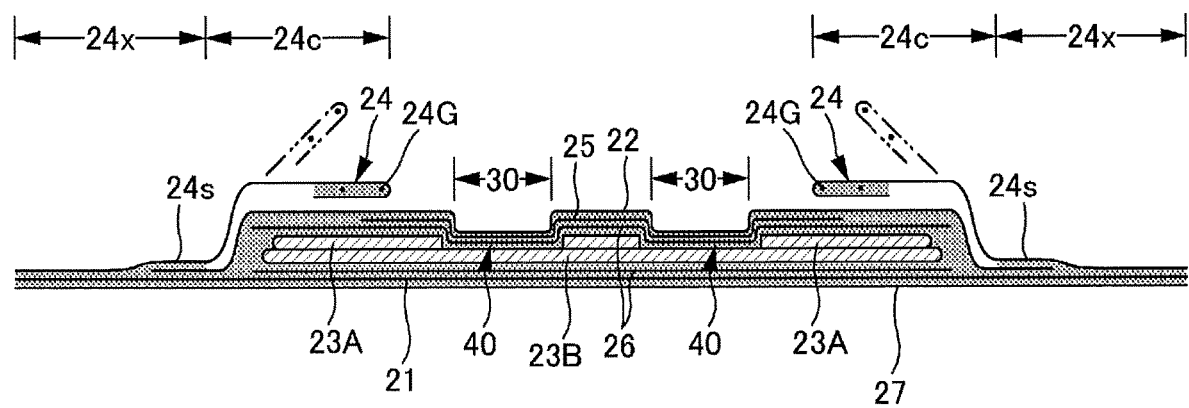
FIG. 4 is a cross-sectional view along X-X line of FIG. 1.
Figure 5:
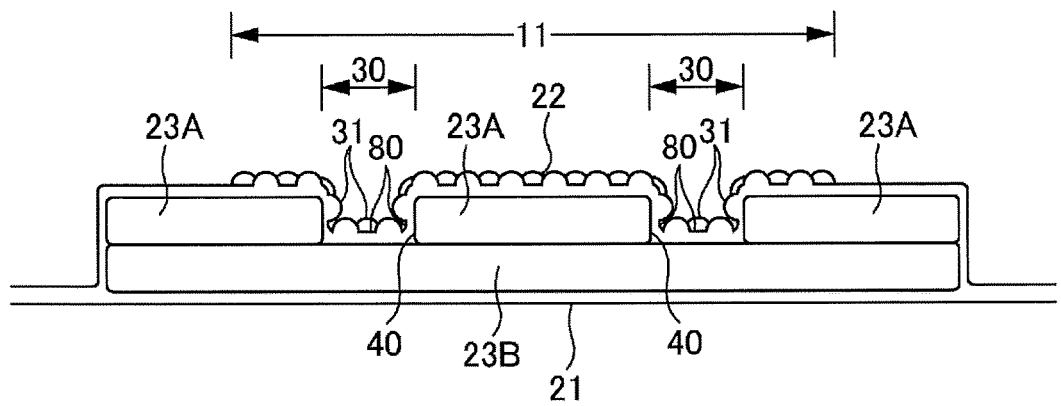
FIG. 5 illustrates a schematic cross-sectional view in a developed state (a) and a schematic plane view in the developed state (b)
Figure 5:
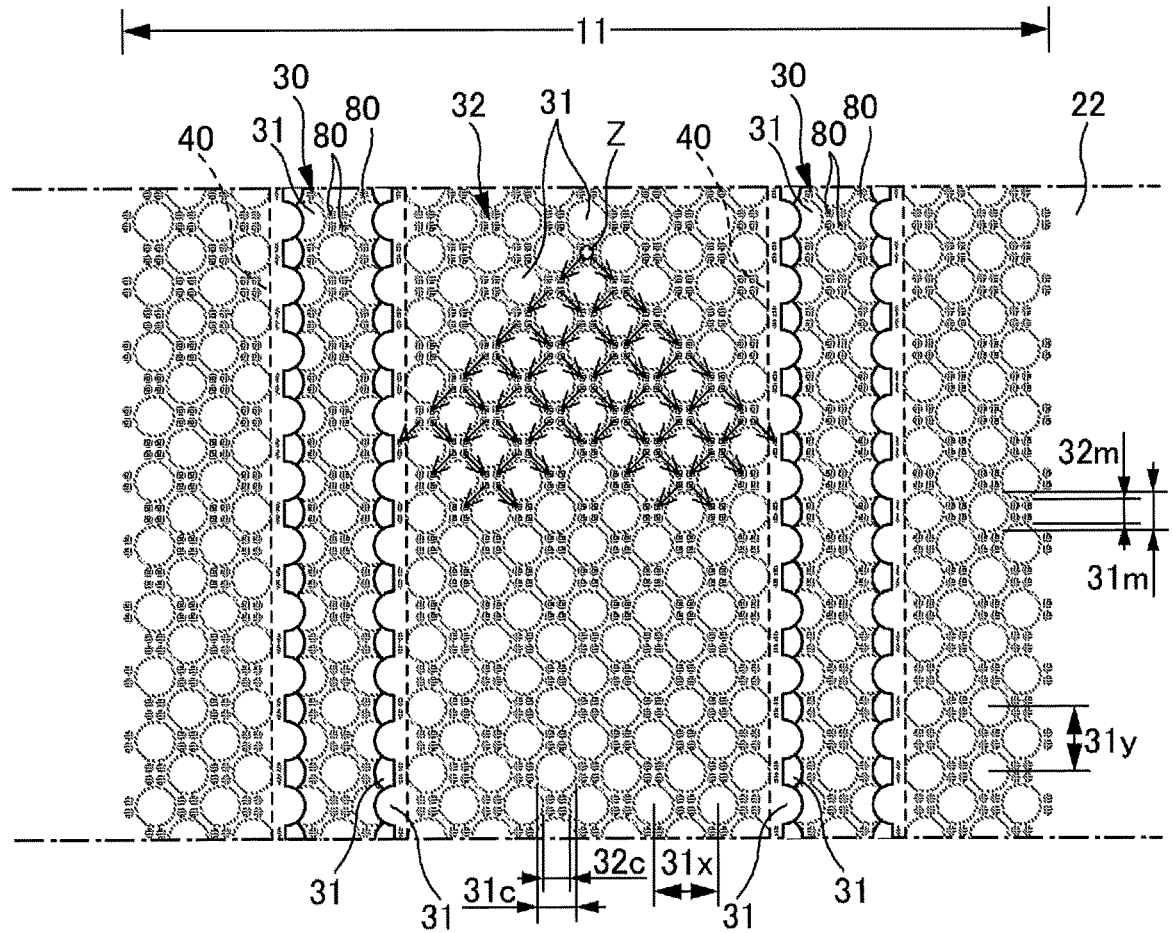

As illustrated in FIG. 3 through FIG. 5, the absorbents 23A and 23B have a two-layer structure formed of a lower layer absorbent 23B and an upper layer absorbent 23A that is formed on the front side of the lower layer absorbent 23B. As the upper layer absorbent 23A and the lower layer absorbent 23B, a stacked body of pulp fibers 23f, an aggregate of filaments, such as cellulose acetate, or nonwoven fabric may be used as a basis, and a resultant obtained by mixing and fixing superabsorbent polymer particles 23p, such as particulates, may be used, if necessary. The lower layer absorbent 23B may preferably be a stack of at least the pulp fibers 23f, and, in particular, the lower layer absorbent 23B may preferably be a mixture of the pulp fibers 23f and the superabsorbent polymer particles 23p. The upper layer absorbent 23A may preferably be a mixture of the pulp fibers 23f and the superabsorbent polymer particles 23p.

As the superabsorbent polymer particles 23p included in the upper layer absorbent 23A and the lower layer absorbent 23B, those used in this type of absorbent products may be used as they are. For example, in a usual case, such as a case in which superabsorbent particles having the same particle size distributions are used for the upper layer absorbent 23A and the lower layer absorbent 23B, superabsorbent polymer particles are desirable such that, when screening is performed (shaking for 5 minutes) using a standard sieve of 500 μm (JIS Z8801-1: 2006), and when screening is performed (shaking for 5 minutes) for the particles falling under this screening sieve using a standard sieve of 180 μm (JIS Z8801-1: 2006), a ratio of the particles remaining on the standard sieve of 500 μm is less than or equal to 30 wt %, and a ratio of the particles remaining on the standard sieve of 180 μm is greater than or equal to 60 wt %. When superabsorbent particles having different particle size distributions are used for the upper layer absorbent 23A and the lower layer absorbent 23B, respectively, the particle size distribution of the superabsorbent polymer particles used for the upper layer absorbent 23A is preferably such that, when screening using the standard sieves of 500 μm and 180 μm is performed, the ratio of the particles remaining on the standard sieve of 500 μm is less than or equal to 50 wt %, and the ratio of the particles remaining on the standard sieve of 180 μm is greater than or equal to 50 wt %; and the particle size distribution of the superabsorbent polymer particles used for the lower layer absorbent 23B is preferably such that, when screening using the standard sieves of 500 μm and 180 μm is performed, the ratio of the particles remaining on the standard sieve of 500 μm is less than or equal to 25 wt %, and the ratio of the particles remaining on the standard sieve of 180 μm is greater than or equal to 70 wt %.

The superabsorbent polymer particles 23p are not particularly limited. However, super absorbent polymer particles 23p with a water absorption rate from 20 seconds to 50 seconds and a water absorption amount from 50 g/g to 80 g/g may preferably be used. As the superabsorbent polymer particles 23p, there are starch-based superabsorbent polymer particles, cellulose-based superabsorbent polymer particles, and synthetic polymer-based superabsorbent polymer particles, and a starch-acrylic acid (salt) graft copolymer, a saponified starch-acrylonitrile copolymer, a crosslinked product of sodium carboxymethyl cellulose, an acrylic acid (salt) polymer, etc., can be used.

The upper layer absorbent 23A and the lower layer absorbent 23B may be integrally or individually enclosed by a packaging sheet 26 with liquid permeability and a liquid reserving property, such as crepe paper, if necessary, for the purpose of retention of a shape and the superabsorbent polymer particles 23p.

The absorbents 23A and 23B extend from the front portion F2 to the rear portion B2. The size of the upper layer absorbent 23A may be the same as the size of the lower layer absorbent 23B. However, as in the depicted embodiment, the total length and the total width of the upper layer absorbent 23A may preferably be less than or equal to those of the lower layer absorbent 23B. In a usual case, the total length of the upper layer absorbent 23A may be approximately from 60% to 90% of the total length of the lower layer absorbent 23B, and the total width of the upper layer absorbent 23A may be approximately from 60% to 90% of the total width of the lower layer absorbent 23B.

The shapes of the upper layer absorbent 23A and the lower layer absorbent 23 may be appropriately defined, and the shapes may be rectangular shapes. However, at least in the larger one of the absorbents 23A and 23B (the lower absorbent 23B in the depicted embodiment), a predetermined part in the middle of the front-rear direction including the crotch portion C2 may preferably be formed as a constriction 23n with a narrow width. The minimum width W5 of the constriction 23n may preferably be approximately from 50% to 65% of a width W2 of a non-constricted portion located in front or behind the constriction 23n. Assuming that the front end of the product is 0% and the rear end of the product is 100%, the front end of the constriction 23n may preferably be located within a range from 10% to 25%, the rear end of the constriction 23n may preferably be located within a range from 40% to 65%, and the portion with the minimum width W5 of the constriction 23n may preferably be located within a range from 25% to 30%.

Figure 2:
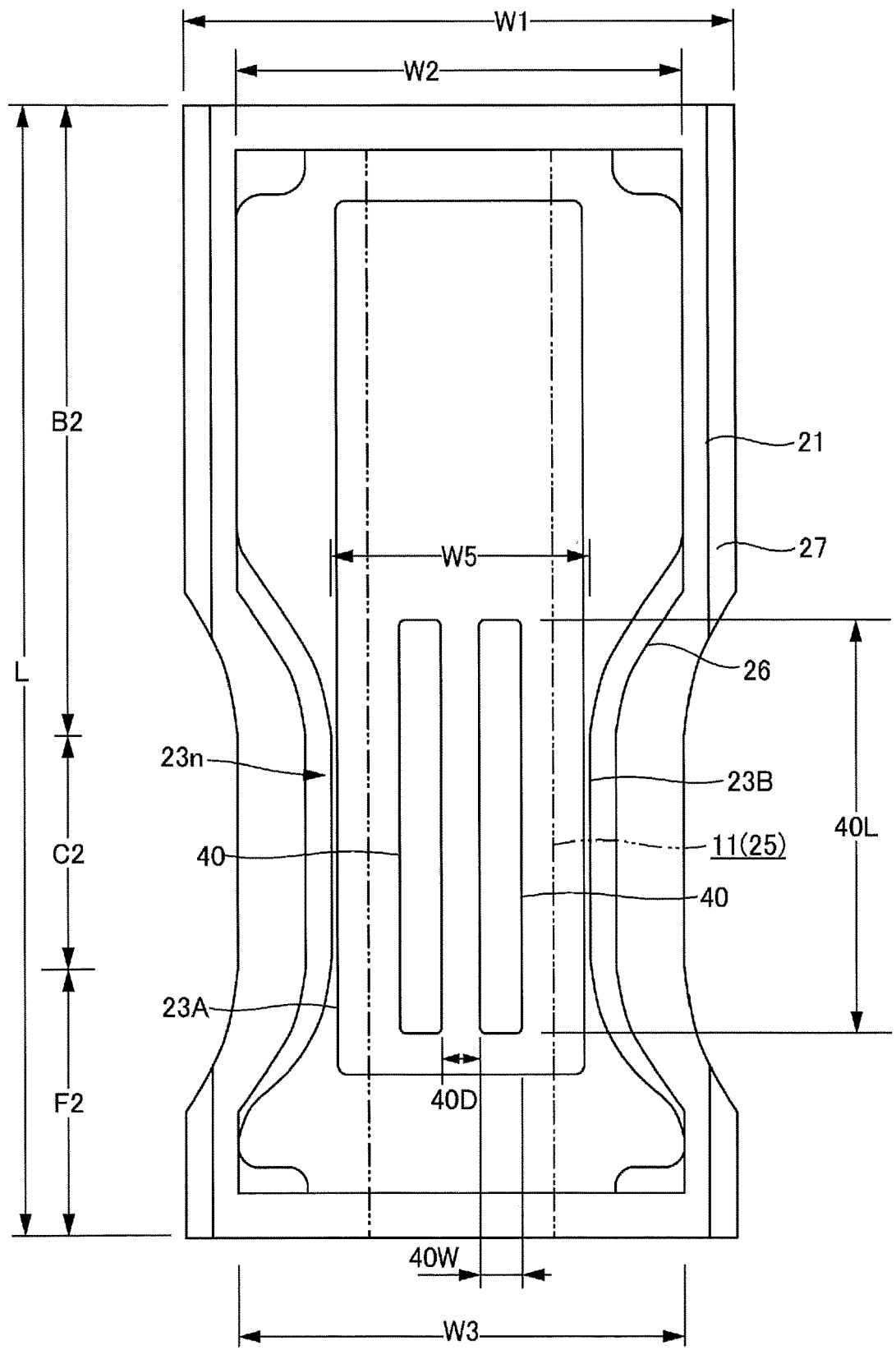
FIG. 2 is a plan view only illustrating main parts.

Characteristically, as illustrated in FIG. 1 and FIG. 2, at least in a region in the front-rear direction corresponding to the crotch portion C2, a pair of right and left slits 40 with predetermined widths are extended in the front-rear direction only in the upper layer absorbent 23A. In addition to the embodiment, as illustrated in FIG. 4 and FIG. 5, in which the slits 40 with the predetermined widths are not formed in the lower layer absorbent 23B (in this case, the lower layer absorbent 23B may have a slit with no width), as illustrated in FIG. 6, an integral slit 40 that passes through the upper layer absorbent 23A and the lower layer absorbent 23B in the width direction may be formed.

Figure 6:
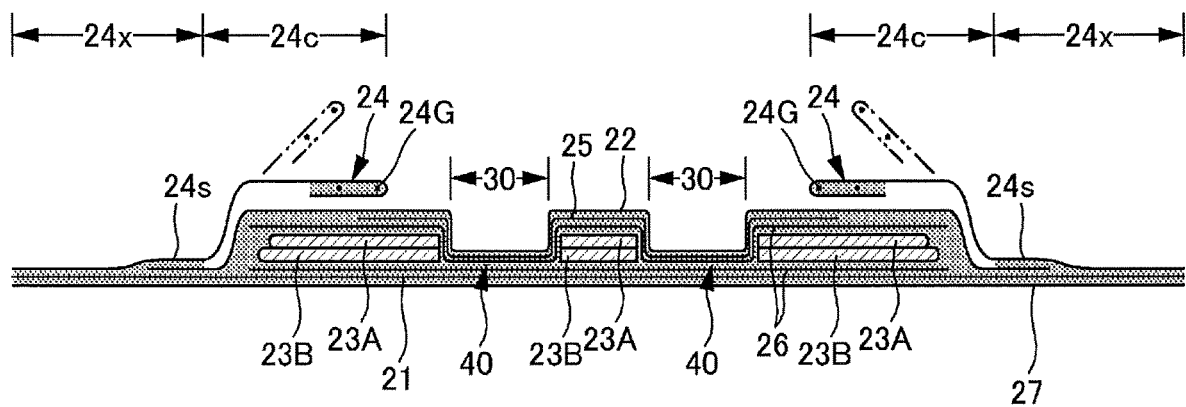
FIG. 6 is a cross-sectional view corresponding to the X-X cross-section of FIG. 1.

As illustrated in FIG. 4 through FIG. 6, the top sheet 22 is provided with depressed portions 30 that fall into the slits 40 of the upper layer absorbent 23A. At least in a region located between the slits 40, a large number of convex portions 31 protruding toward the front side are arranged in a zigzag shape (alternate arrangement in adjacent rows) while spaced apart by intervals. An interval 32c of the convex portions 31 adjacent in the width direction is shorter than sizes 31c in the width direction of the convex portions located in front and behind the portion of the interval 32c. In the depicted embodiment, the intermediate sheet 25 and a front side portion of the packaging sheet 26 exist between the top sheet 22 and the upper layer absorbent 23A. Accordingly, the intermediate sheet 25 and the front side portion of the packaging sheet 26 also fall into the slits 40 together with the top sheet 22. The intermediate sheet 25 may be omitted.

Figure 9:
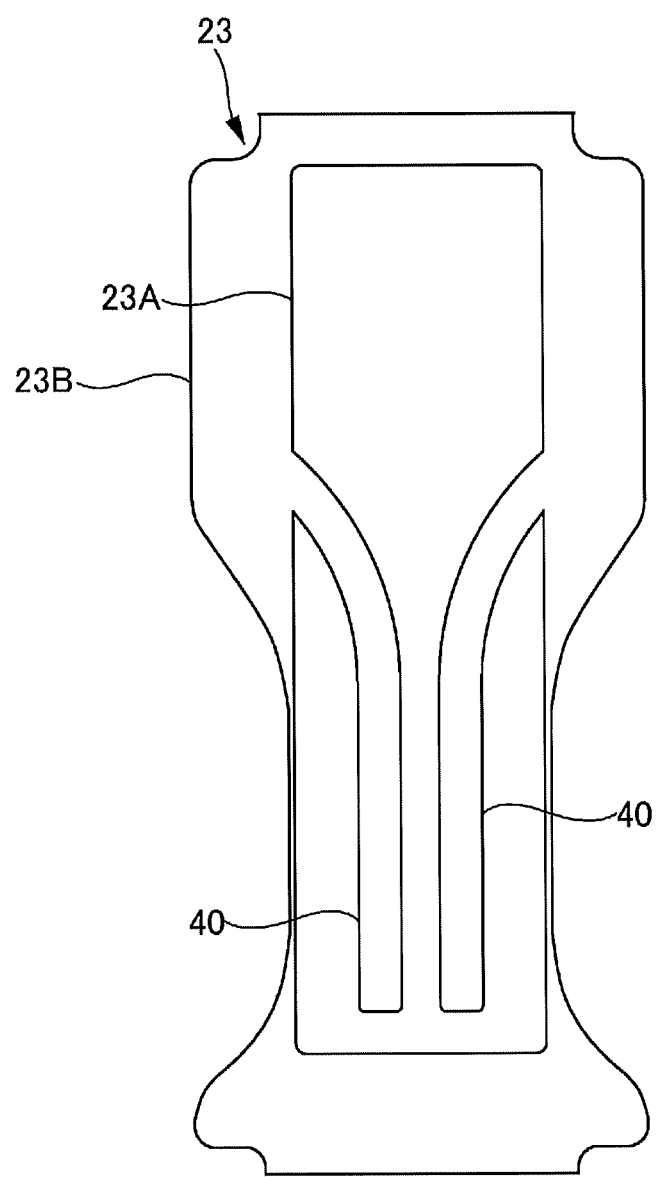
FIG. 9 is a plan view of another absorbent.

A length 40L in the front-rear direction of the slits 40 is not particularly limited, provided that the slits 40 are provided in the crotch portion C2. Accordingly, the slits 40 may be formed over the entire portion in the front-rear direction of the upper layer absorbent 23A. However, as in the depicted embodiment, the slits 40 may preferably be extended from a crotch side end portion of the front portion F2 to a crotch side end portion of the rear portion B2. Additionally, as illustrated in FIG. 9, the rear side portions of the slits 40 may be bent, so that the rear side portions are directed toward outside in the width direction (the front side may also be bent in the same manner). More specifically, assuming that the front end of the disposable diaper 200 is 0% and the rear end of the disposable diaper 200 is 100%, the front ends of the slits 40 may preferably be located within a range from 15% to 30%, and the rear ends of the slits 40 may preferably be located within a range from 40% to 70%.

In the upper layer absorbent 23A of the depicted embodiment, the front and rear ends of the slits 40 do not pass through the fringe of the upper layer absorbent 23A. However, as in the example illustrated in FIG. 9, the rear ends (which may be the front ends or both ends) may reach the fringe. In the embodiment in which the front and rear ends of the slits 40 reach the side ends of the upper layer absorbent 23A, each portion lateral to the corresponding slit 40 is separated from the portion between the slits 40.

The slits 40 are spaced apart in the width direction by an interval, and one slit 40 is provided on each of left and right sides. In this case, the positions of the slits 40 in the width direction may preferably be bilateral symmetry. A pad type disposable diaper may be generally configured such that the width of the absorbent is wider than the crotch width of the wearer, both end portions in the width direction of the crotch portion are facing the inner thighs of the wearer, and the middle portion in the width direction is the portion facing the crotch. Accordingly, it is desirable to provide slits along the boundaries of these parts. Thus, in a usual case, the interval 40D of the slits 40 may preferably be approximately from 10% to 30% of the minimum width W5 of the constriction 23n of the absorbents 23A and 23B.

The width 40W of the slit 40 is not particularly limited, provided that side walls facing each other are spaced apart. However, in a usual case, the width 40W of the slit 40 may preferably be approximately from 10% to 20% of the minimum width W5 of the constriction 23n of the absorbents 23A and 23B. Specifically, the width 40W of the slit 40 may be approximately from 5 mm to 32 mm for adult products.

In the pad type disposable diaper 200 configured as described above, the region located between the slits 40 in the top sheet 22 is a urine discharge position or located behind the urine discharge position, which is a location at which a larger amount of urine is supplied by the slope toward the crotch. Here, as illustrated in (b) of FIG. 5, at least in the region located between the slits 40, a large number of the convex portions 31 are arranged in a zigzag manner while spaced apart by intervals, and the interval 32 of the convex portions 31 adjacent in the width direction is shorter than the sizes 31c in the width direction of the convex portions 31 located in front and behind the interval 32. As a result, the concave portions 32 between the adjacent convex portions 31 do not linearly continue in the front-rear direction, and the concave portions 32 continue in an oblique lattice pattern. Accordingly, urine supplied to the region located between the slits 40, for example, at the position Z, tends to flow diagonally rearward compared to the front-rear direction, as indicated by the arrows. As a result, when urine flows rearward from the urine discharge position, the urine tends to flow into the slits 40 on both sides in the width direction. Accordingly, by providing the slits 40 only on both sides in the width direction, while suppressing the decrease in the absorption capacity, the crotch fitting characteristics with respect to the crotch portion C2 can be enhanced, and the reversion prevention property can be enhanced.

The large number of the convex portions 31 arranged in a zigzag manner can be formed by pressing the top sheet 22 from the rear side toward the front side using emboss processing. Alternatively, portions compressed in the thickness direction (which includes, for example, in addition to the compressed portions 80 described below, the low transmission portions 80, such as those of the depicted embodiment) may be formed, at least, at three sides, preferably four sides, around the position to be the convex portion 31, and a portion surrounded by concave portions 32 connecting the compressed portions may be formed as the convex portion 31 that relatively protrudes.

The shape of the convex portion 31 may preferably be a circular dome shape. However the shape of the convex portion 31 may be a suitable shape, such as an elliptical dome shape or a polygonal dome shape. In particular, the shape of the convex portion 31 may preferably be a shape extended in the width direction so as to enhance diffusibility in the width direction. Here, the convex portion 31 can be formed by emboss processing of the top sheet 22.

The size and an arrangement interval of the convex portion 31 may be appropriately determined, provided that the interval 32c of the convex portions 31 adjacent in the width direction is shorter than the sizes 31c in the width direction of the convex portions 31 located in front and behind the portion of the interval 32c (in other words, the size 31c in the width direction of the convex portion 31 is greater than the intervals 32c between the adjacent convex portions 31 arranged in the width direction in front and behind the convex portion 31). However, the interval 32c between the convex portions 31 adjacent in the width direction may preferably be approximately from 0.5 to 0.8 times the sizes 31 in the width direction of the convex portions 31 located in front and behind the portion of the interval 32c. Additionally, an interval 32m between the convex portions 31 adjacent in the front-rear direction may preferably be shorter than the sizes 31m in the front-rear direction of the convex portions 31 located on both sides of the width of the portion of the interval 32m (in other words, the size 31m in the front-rear direction of the convex portion 31 is greater than the interval 32m between the convex portions 31 arranged in the front-rear direction adjacent to both sides in the width direction of the convex portion 31). In particular, the interval 32m between the adjacent convex portions 31 in the front-rear direction may preferably be from 0.5 to 0.8 times the sizes 31m in the front-rear direction of the convex portions 31 located on both sides of the width of the portion of the interval 32m.

As specific examples of the sizes, the size 31m in the front-rear direction of the convex portion 31 may preferably be from 3.6 mm to 5.6 mm; the size 31c in the width direction of the convex portion 31 may preferably be from 4.0 mm to 6.0 mm; and the size 31m in the front-rear direction of the convex portion 31 may preferably be from 0.9 to 1.0 times the size 31c in the width direction of the convex portion 31. Furthermore, the center interval 31y between the convex portions 31 in the front-rear direction in the sequence of the convex portions 31 arranged in the front-rear direction may preferably be from 6.2 mm to 9.7 mm; the center interval 31x between the convex portions 31 in the width direction in the sequence of the convex portions 31 arranged in the width direction may preferably be from 6.9 mm to 10.5 mm; and the center interval 31y in the front-rear direction may preferably be from 0.8 to 1.0 times the center interval 31x in the width direction. Furthermore, in a usual case, the height 31z of the convex portion 31 may preferably be approximately from 0.8 mm to 2 mm.

The convex portions 31 may be formed only in the region located between the slits 40, provided that the convex portions 31 are formed over the entire region located between the slits 40. However, it is difficult to form the convex portions 31 to be accurately adjusted to the locations of the slits 40. Accordingly, as illustrated in FIG. 5, the convex portions 31 may preferably be formed over a region 11 (for example, a region that is wider than the region located between the slits 40 in at least one of the width direction and the front-rear direction) of the top sheet 22 that includes the region located between the slits 40 and that is wider than the region located between the slits 40, and the convex portions 31 may be formed over the entire top sheet 22. In particular, as in the depicted embodiment, the front ends of the slits 40 may preferably be separated rearward from the front ends of the absorbents 23A and 23B, and the region in which the convex portions 31 are arranged may preferably be extended to the front sides of the slits 40. When the wearer is in a prone position or in a side lying position, the inclination of the top sheet 22 may fall forward. In such a case, front leakage may occur. However, by extending the region in which the convex portions are arranged to the front sides of the slits 40, the diffusibility in the front-rear direction in the front sides of the slits 40 can be lowered, and the diffusion to the oblique front side can be promoted, so as to prevent the front leakage. As in the depicted embodiment, the convex portions 31 may preferably be formed in the depressed portion 30. As described above, if the convex portions 31 are formed in the depressed portions 31, even if the crotch portion C2 is nipped between legs of the wearer and the absorbents 23A and 23B shrink to some extent in the width direction so that the slits 40 are collapsed in the width direction, gaps are maintained around the convex portions 31 and the enhancement in the diffusibility in the slits is not easily damaged.

Figure 7:
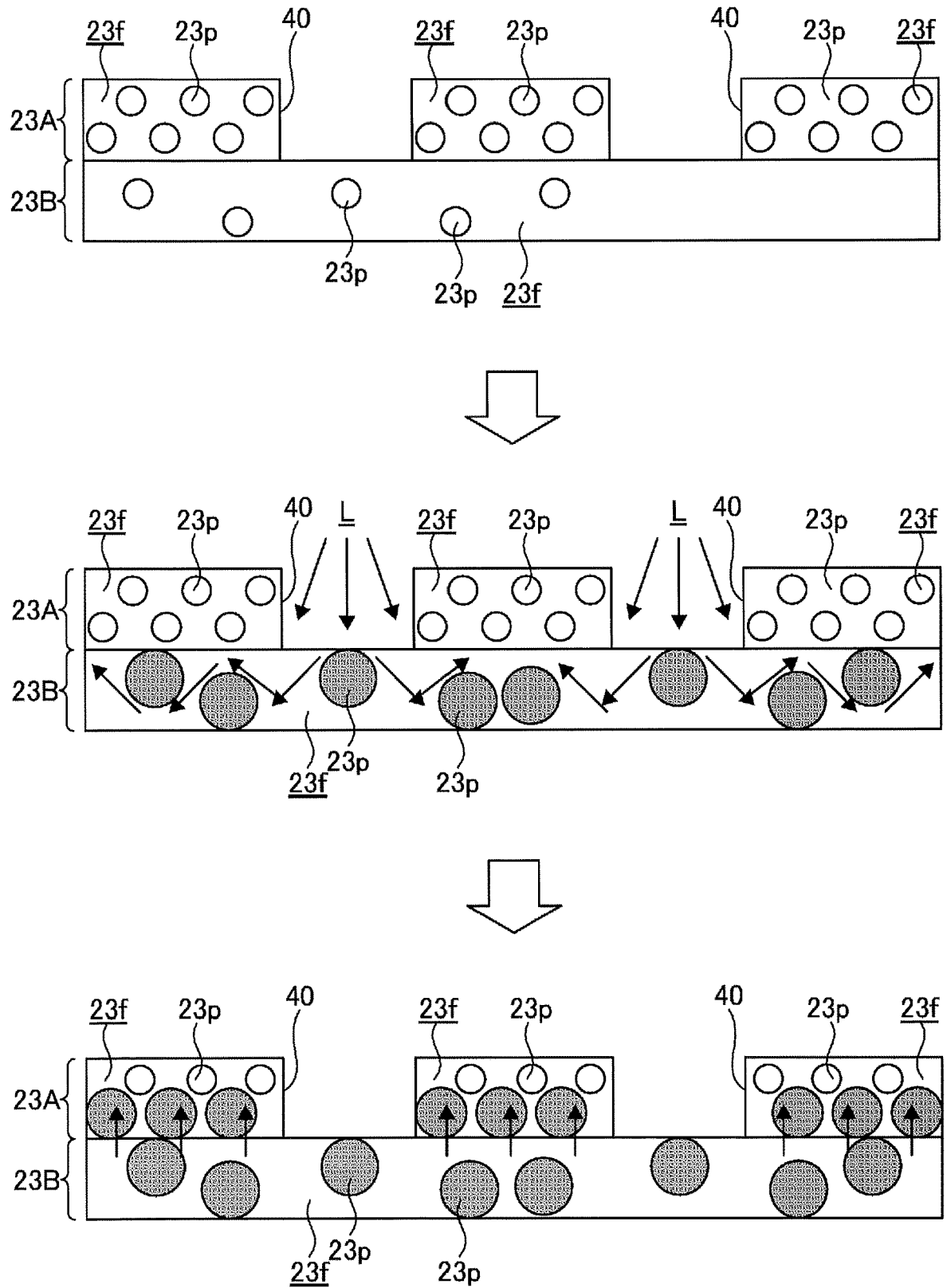
FIG. 7 is a cross-sectional view schematically illustrating an absorption mechanism of an absorbent.
Figure 8:
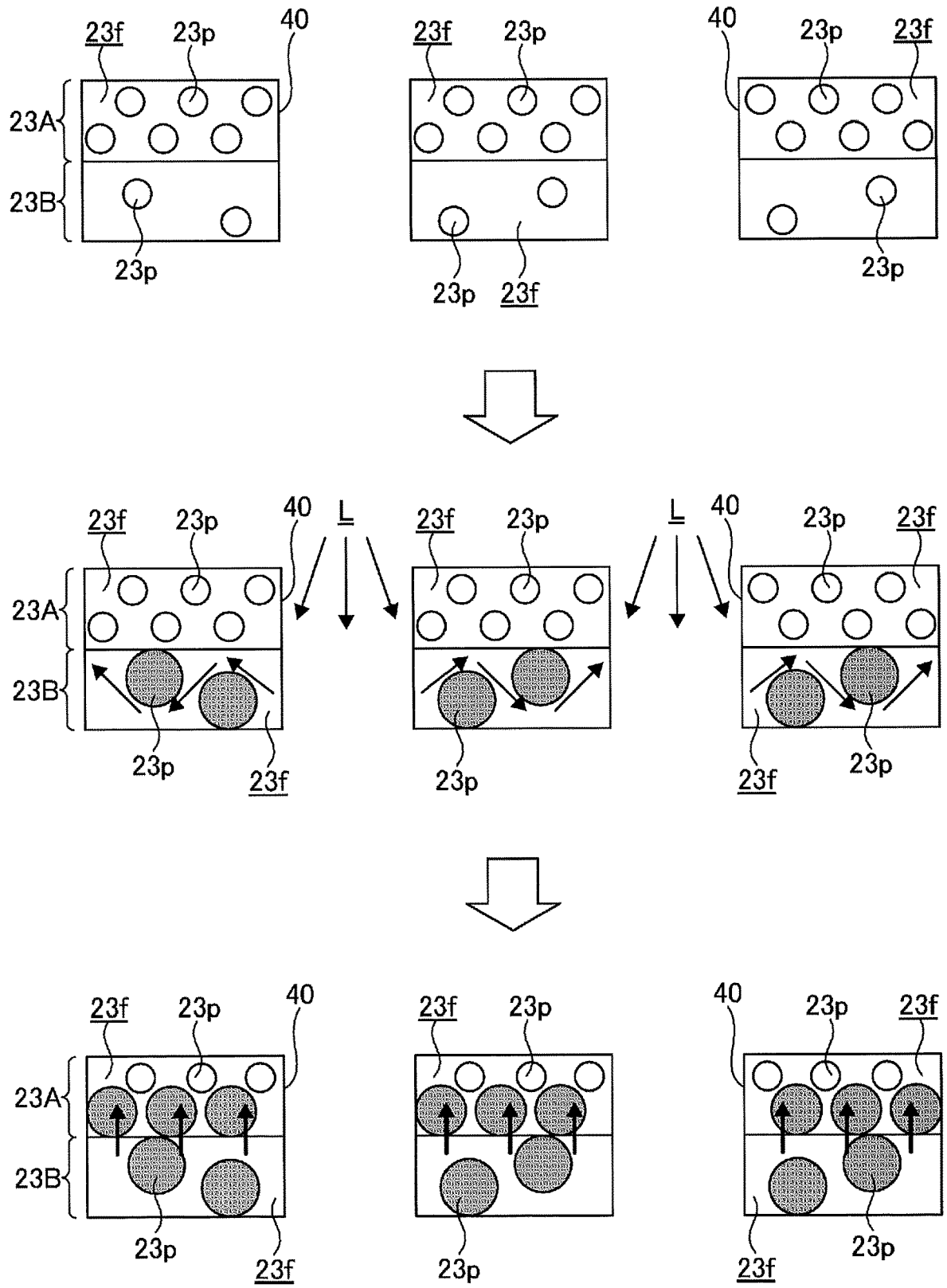
FIG. 8 is a cross-sectional view schematically illustrating the absorption mechanism of the absorbent.

Furthermore, as illustrated in FIG. 7 and FIG. 8, the weight ratio of the superabsorbent polymer particles 23p with respect to the pulp fibers 23f in the upper layer absorbent 23A may preferably be greater than the weight ratio of the superabsorbent polymer particles 23p with respect to the pulp fibers 23f in the lower layer absorbent 23B. Namely, as the changes in the absorption state illustrated in FIG. 7 and FIG. 8, in the absorbents 23A and 23B, the liquid component L of excrement is preferentially supplied to the lower layer absorbent 23B through the slits 40, though the liquid component L of excrement is also supplied to the upper layer absorbent 23A. Here, if the weight ratio of the superabsorbent polymer particles 23p with respect to the pulp fibers 23f in the lower layer absorbent 23B is lower than that of the upper layer absorbent 23A, gel blocking tends not to occur compared to the upper layer absorbent 23A, and the liquid component L diffuses wider in the lower layer absorbent 23B. In the figures, the movement of the liquid component is indicated by arrows. Then, after saturation of the absorption at least by the lower layer absorbent 23B, the liquid component absorbed by the lower layer absorbent 23B is suctioned by the upper layer absorbent 23A to be moved to the upper layer absorbent 23A, and the liquid component is absorbed and retained by the upper layer absorbent 23A. At this time, until at last, the absorption capacity is left at the surface side (skin side) of the upper layer absorbent 23A because, in the upper layer absorbent 23A, the weight ratio of the superabsorbent polymer particles 23p with respect to the pulp fibers 23f is high and a larger amount of the liquid component can be absorbed and retained, while the lower layer absorbent 23B preferentially absorbs the liquid component. As a result, the reversion prevention property can further be enhanced. Note that, in FIG. 7 and FIG. 8, the sizes of the superabsorbent polymer particles 23p are exaggerated so as to facilitate understanding of the content ratio and absorption/expansion change of the superabsorbent polymer particles 23p.

Considering such an absorption mechanism, the superabsorbent polymer particles 23p included in the lower layer absorbent 23B may preferably be superior in liquid permeability, specifically, the absorption rate may preferably be from 20 seconds to 30 seconds and the absorption amount may preferably be from 50 g/g to 70 g/g; and the superabsorbent polymer particles 23p included in the upper layer absorbent 23A may preferably have a large absorption amount, specifically, the absorption rage may preferably be from 60 seconds to 80 seconds and the absorption amount may preferably be from 50 g/g to 80 g/g.

When the weight ratio of the superabsorbent polymer particles 23p with respect to the pulp fibers 23f in the upper layer absorbent 23A is greater than the weight ratio of the superabsorbent polymer particles 23p with respect to the pulp fibers 23f in the lower layer absorbent 23b, the weight ratio of the superabsorbent polymer particles 23p with respect to the pulp fibers 23f in the upper layer absorbent 23A and the weight ratio of the superabsorbent polymer particles 23p with respect to the pulp fibers 23f in the lower layer absorbent 23B may be suitably determined. However, if the total basis weight of the upper layer absorbent 23A (total of the pulp 19f and the superabsorbent polymer particles 23p) is from 350 g/m2 to 700 g/m2, the weight ratio of the superabsorbent polymer particles 23p with respect to the pulp fibers 23f in the upper layer absorbent 23A may preferably be approximately from 55% to 100%, particularly preferably from 65% to 90%. Furthermore, if the total basis weight of the lower layer absorbent 23b (total of the pulp 19f and the superabsorbent polymer particles 23p) is from 250 g/m2 to 7450 g/m2, the weight ratio of the superabsorbent polymer particles 23p with respect to the pulp fibers 23f in the lower layer absorbent 23B may preferably be approximately from 0% to 50%, particularly preferably from 30% to 40%.

When the top sheet 22 is formed of thermoplastic nonwoven fabric, the low transmission portion 80, in which fibers in a compressed state in the thickness direction are mutually welded, may preferably be formed between the adjacent convex portions 31 (i.e., the concave portion 32) in the top sheet 22. The low transmission portion 80 is a portion in which the fibers are welded to each other in a state in which the nonwoven fabric of the top sheet 22 is compressed in the thickness direction and the liquid permeability is lower than that of the surrounding. To this extent, in addition to a portion in which fiber gaps remain and that shows some permeability, a portion that almost completely becomes a film and that does not transmit any liquid is included in the low transmission portion 80. If a large number of such low transmission portions 80 are provided between the convex portions 31 of the top sheet 22, the permeability is restricted, and the diffusibility is enhanced correspondingly. As a result, urine on the top sheet 22 is facilitated to pass through between the convex portions 31 to flow into the slits 40.

Figure 10:
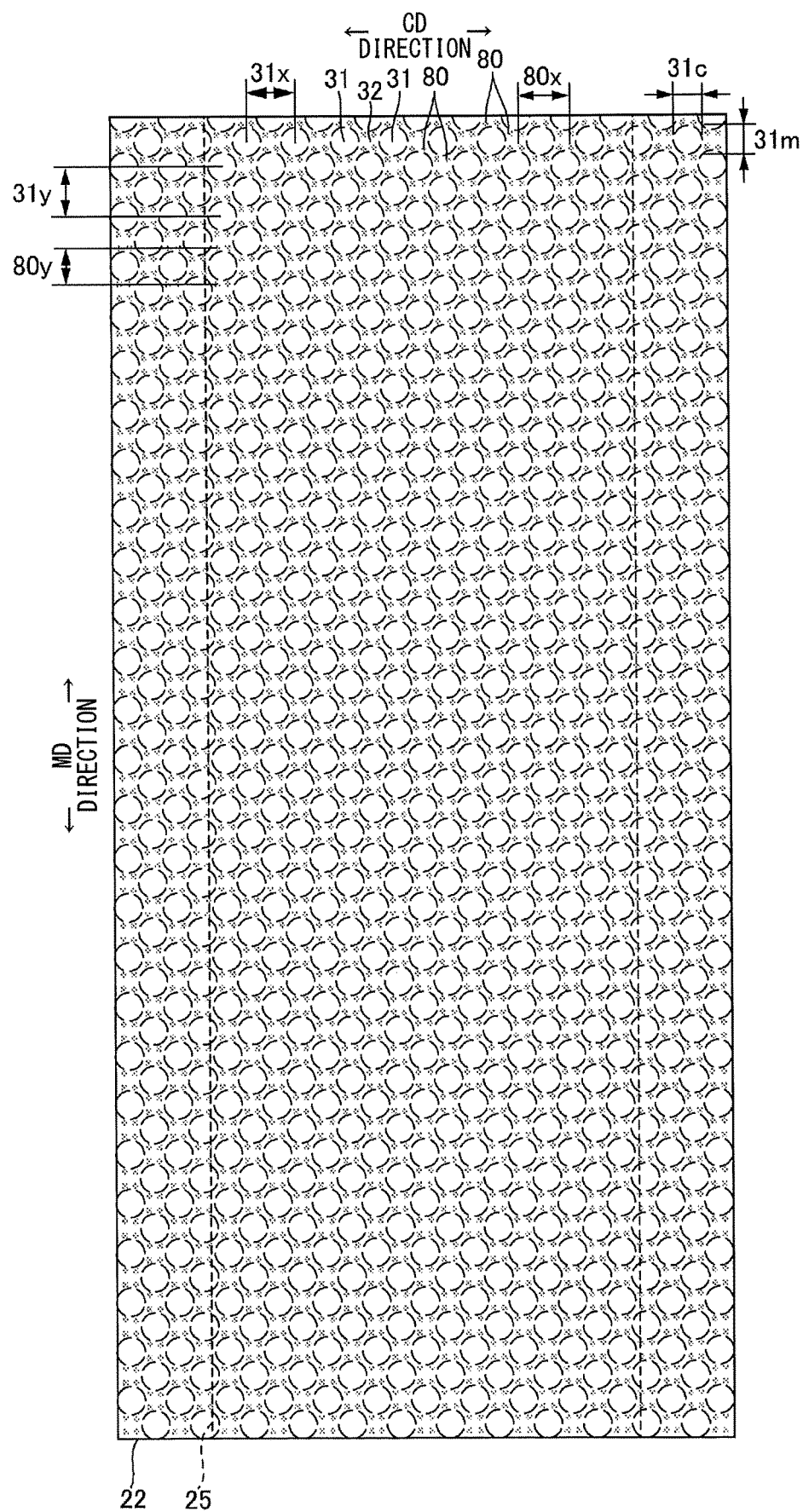
FIG. 10 is a plan view of a top sheet and a second sheet.
Figure 11:
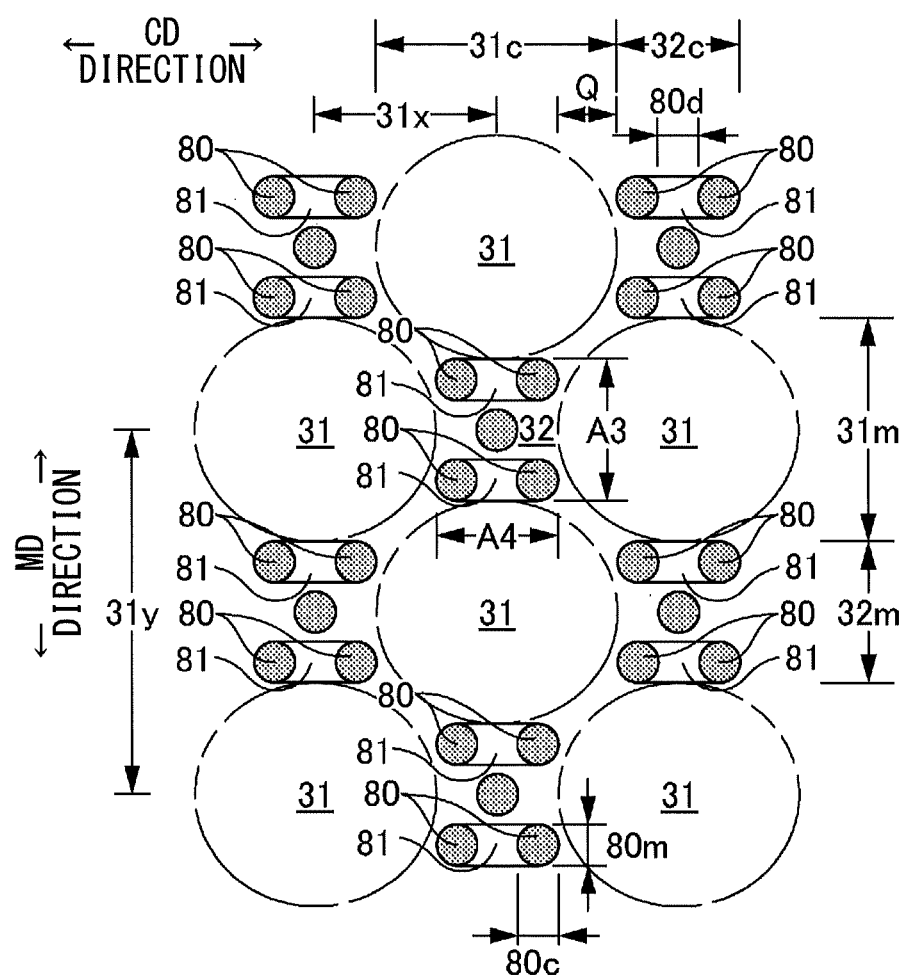
FIG. 11 is an enlarged plan view of a pattern of convex portions and low transmission portions.

The low transmission portions 80 may be formed continuously in an oblique lattice shape, as illustrated in (a) of FIG. 21, for example. However, the flexibility of the top sheet 22 may be damaged. Accordingly, the low transmission portions 80 may preferably be formed while spaced apart by intervals, as illustrated in FIG. 10, FIG. 11 and (b) of FIG. 21. In this case, if the area ratio of the low transmission portions 80 (the ratio of the total area of the low transmission portions 80 in the region located between the slits 40 to the total area of the region located between the slits 40) is too small, the effect of enhancing the diffusibility becomes insufficient. Thus, the area ratio of the low transmission portions 80 may preferably be greater than or equal to 4%, more preferably greater than or equal to 7%.

The shape of each of the low transmission portions 80 may be suitably determined, such as a circular shape (see (b) of FIG. 21), an elliptical shape, a square shape, a rectangular shape, a linear shape, other polygonal shapes, a crescent shape, a star shape, a cloud shape, etc.

The size of the low transmission portion 80 can be suitably determined. When the low transmission portions 80 are discontinuously formed in the front-rear direction, the length of the low transmission portion 80 in the front-rear direction (for example, the reference numeral 80m of the embodiment described below) may be from 0.5 mm to 3.0 mm, in particular, approximately from 0.7 mm to 1.1 mm. In a usual case, the width of the low transmission portion 80 (for example, the reference numeral 80c of the embodiment described below) may be from 0.5 mm to 3.0 mm, in particular, approximately 0.7 mm to 1.1 mm. Additionally, when the low transmission portions 80 are discontinuously formed in the front-rear direction, the area of each low transmission portion 80 may be from 0.19 mm$^2$ to 1.7 mm$^2$, in particular, approximately from 0.38 mm$^2$ to 0.95 mm$^2$. Additionally, when a plurality of sequences of the low transmission portions 80 is formed in the width direction, the distance between the centers of the adjacent sequences may be greater than the width of the sequence, preferably approximately from 1 to 5 times as large as the width of the sequence. In a usual case, the distance between the centers of the adjacent sequences may be approximately from 0.5 mm to 15 mm.

The low transmission portions 80 may be formed in the entire area in which the convex portions 31 are arranged, or may be formed only in a part of the area in which the convex portions 31 are arranged. In particular, in the embodiment in which the slits 40 are formed only in the upper layer absorbent 23A, if a large number of the low transmission portions 80 are formed in the depressed portions 30, the diffusibility of urine in the slits 40 is enhanced, the permeability in the depressed portions 30 is restricted, and the diffusibility is enhanced correspondingly. Namely, according to this configuration, by forming the slits 40 in the upper layer absorbent 23 without forming the slits 40 in the lower layer absorbent 23B, the absorbable capacity can be reserved as much as possible. At the same time, by scattering the low transmission portions 80, the diffusibility of urine in the slits 40 can be enhanced. As a result, saturation of absorption may hardly occur, and the absorption rate can be increased.

The arrangement and the number of the low transmission portions 80 with respect to the convex portions 31 are not particularly limited, provided that the low transmission portions 80 are arranged between the convex portions 31. However, as in the examples illustrated in FIG. 10, FIG. 11, and (b) of FIG. 21, the low transmission portions 80 may preferably be arranged such that one or dense multiple of the low transmission portions 80 are arranged at each of the four sides (front, rear, left, and right) of the concave portion 31. The arrangement of the low transmission portions 80 may be irregular; however, the arrangement of the low transmission portions 80 may preferably be a regular pattern as a whole.

The low transmission portions 80 may be formed in any form. For example, by applying a heat emboss process to the top sheet 22 in a single state, the low transmission portions 80 can be formed in a state in which the low transmission portions 80 are not adhered to the component on the rear side by welding of the fibers. However, since the low transmission portions 80 are portions at which the fibers are welded, it is preferable to secure the top sheet 22 to the component on the rear side using this. In this case, the portions between the low transmission portions 80 are not compressed and become the convex portions 31 that protrude toward the front side.

FIG. 10 through FIG. 13 shows an example of a configuration which also serves as this bonding. Namely, by bonding the portions of the top sheet 22 between the convex portions 31 adjacent in the width direction and in the front-rear direction to the intermediate sheet 25 by pressure welding, a large number of the low transmission portion 80 is formed to have a discontinuous pattern in the width direction and in the front-rear direction. The low transmission portions 80 are also parts forming the bottom parts of the concave portions 32. Characteristically, in the bonding pattern of the top sheet 22 and the intermediate sheet 25, in the region between the convex portions 31 adjacent in the MD direction, a sequence obtained by arranging a plurality of low transmission portions 80 in the CD direction while spaced apart by intervals is formed to cross the center position in the CD direction of the region. At the same time, at the interval portions of the low transmission portions 80 in the CD direction, the top sheet 22 and the intermediate sheet 25 are not welded, and compressed portions 81 are formed at which the top sheet 22 is compressed compared to the both sides in the MD direction. At the compressed portion 81, the intermediate sheet 25 may or may not be integrally compressed with the top sheet 22, provided that the top sheet 22 is compressed. Additionally, at portions other than the low transmission portions 80 and the compressed portions 81, the top sheet 22 and the intermediate sheet 25 may not be welded and may be compressed in the same manner as the interval portions in the CD direction. However, it is preferable that the top sheet 22 and the intermediate sheet 25 be not welded, and the top sheet 22 be not compressed (which includes an uncompressed state in which the top sheet 22 is not compressed at all) compared to the interval portions in the CD directions. Namely, assuming that the thickness of the low transmission portion 80 of the top sheet 22 is T1, the thickness of the compressed portion 81 is T2, and the thickness of the portion other than the low transmission portion 80 and the compressed portion 81 is T3, T1<T2=T3 may be satisfied. However, T1<T2<T3 is desirable. In the depicted embodiment, a space is formed between the portion of the top sheet 22 including the convex portion 31 and the intermediate sheet 25. However, such a space may not be formed. In this case, the rear surface of the top sheet 22 and the intermediate sheet 25 may be adhered over the entire surface.

Figure 12:
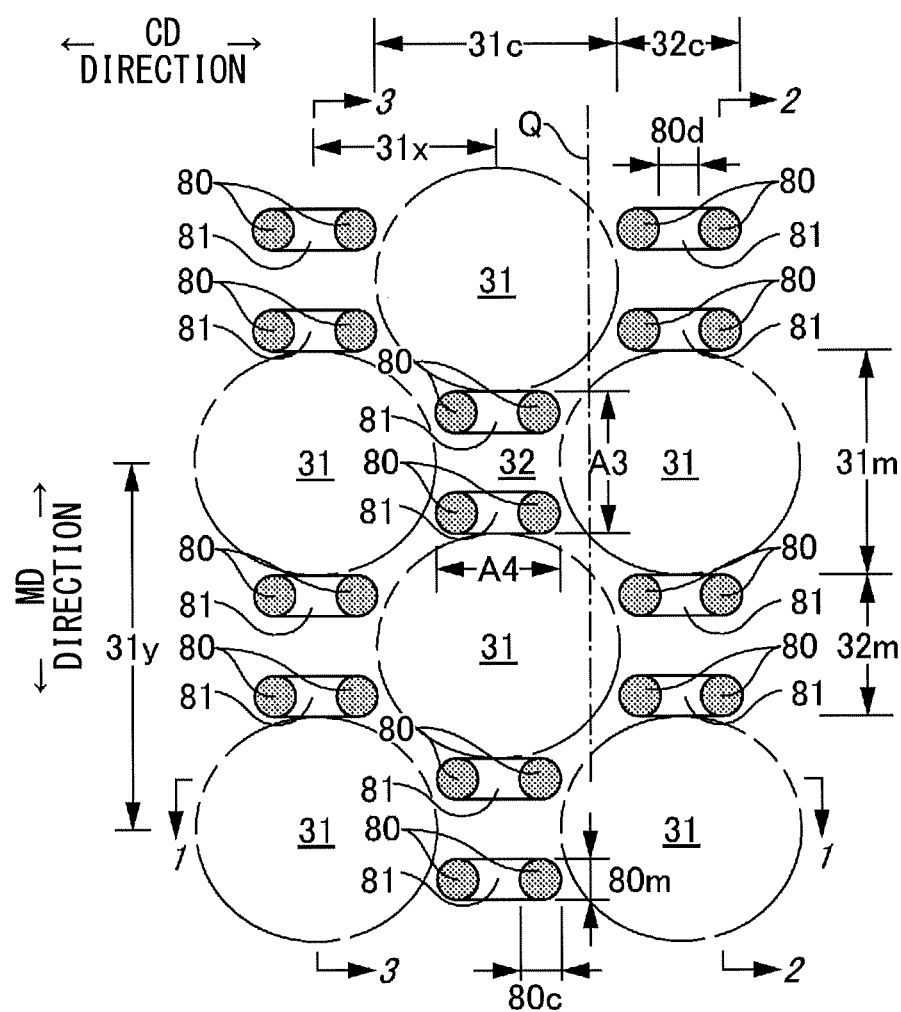
FIG. 12 is an enlarged plan view of a pattern of the convex portions and low transmission portions.
Figure 13:
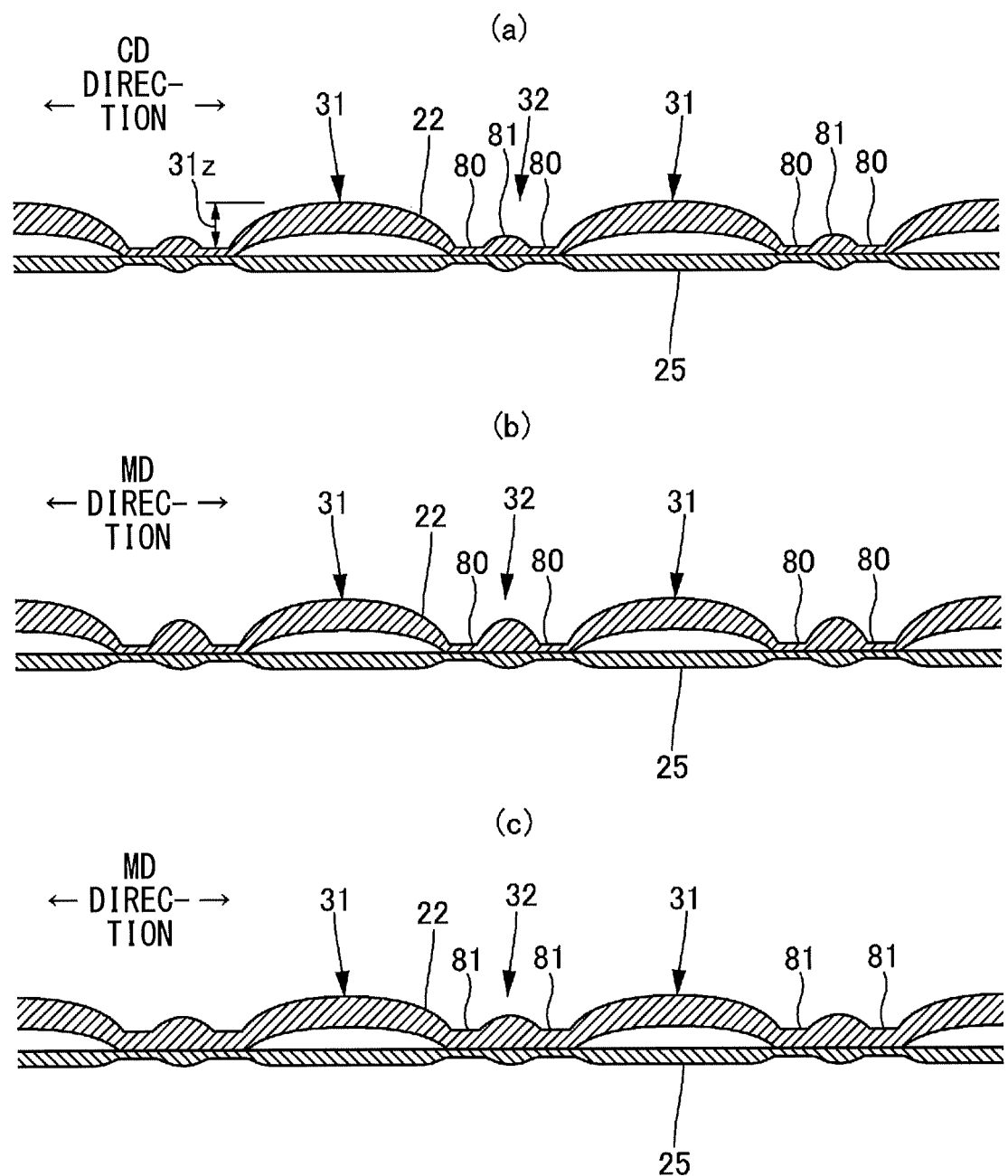
FIG. 13 is a cross-sectional view illustrating a cross section along 1-1, a cross section along 2-2, and a cross section along 3-3 of FIG. 12.
Figure 15:
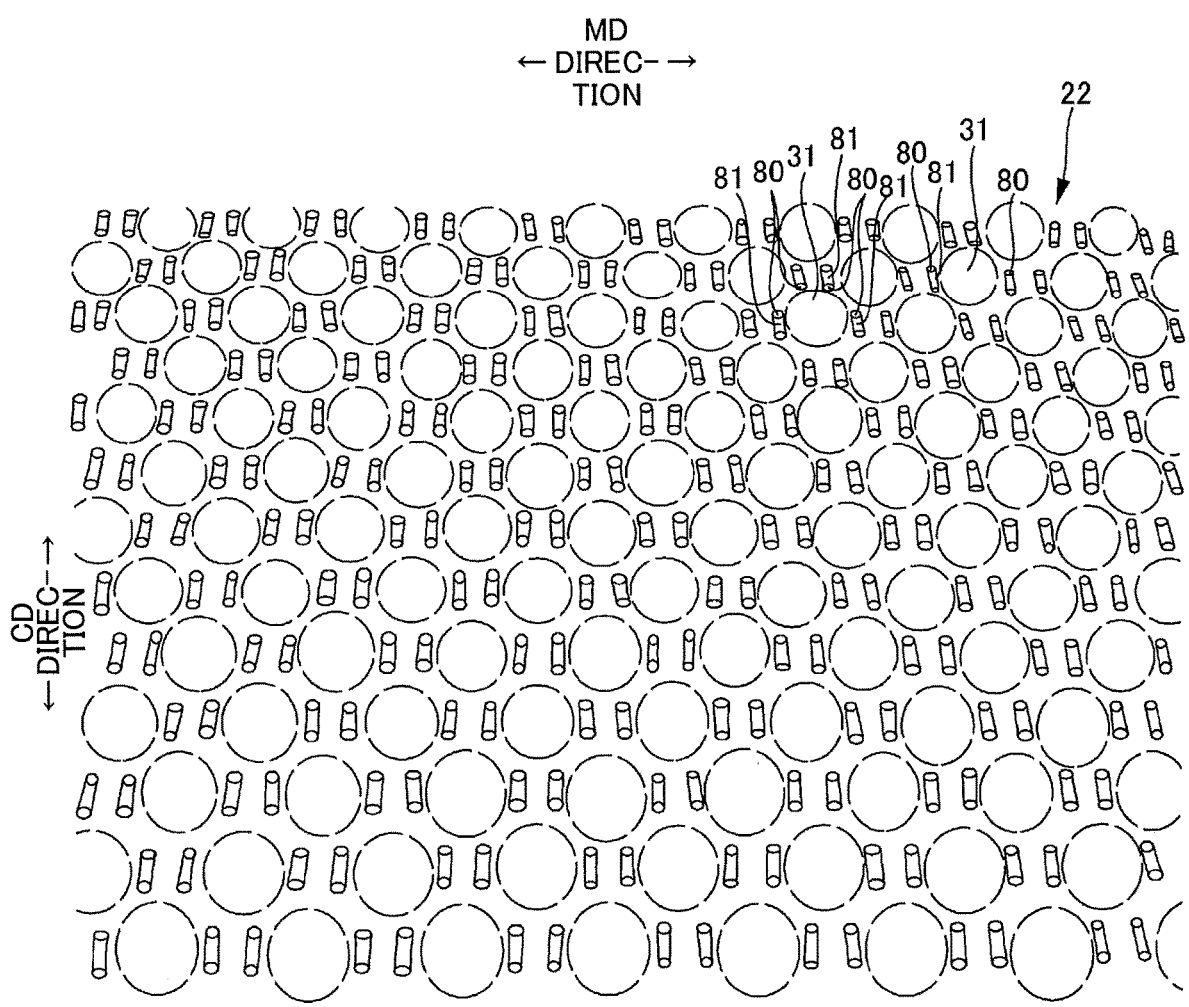
FIG. 15 is a schematic diagram in which an assembly of the top sheet and the second sheet is viewed from an approximate upper side.
Figure 16:
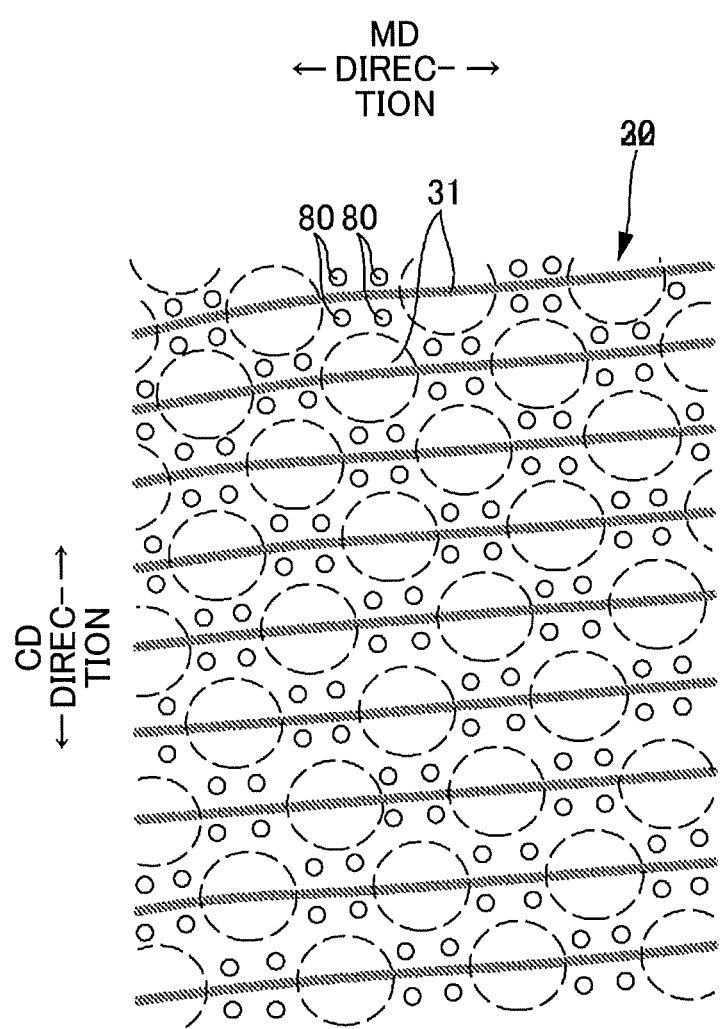
FIG. 16 is a schematic diagram illustrating a surface of a top sheet of a reference sample.

FIG. 15 is a diagram depicting a surface state of a sample obtained by bonding the top sheet 22 and the intermediate sheet 25 adopting the patterns shown in FIG. 10 and FIG. 12. As is clear from the comparison between the sample shown in FIG. 15 and the sample shown in FIG. 16, by adopting, in this manner, a characteristic bonding pattern between the convex portions 31 adjacent in the MD direction, even if vertical wrinkles are formed at the time of forming the convex portions 31, the low transmission portions 80 formed by pressure welding and the compressed portions 81 compressed without being welded are alternately continued in the CD direction so as to traverse the vertical wrinkles during bonding to the intermediate sheet 25. Accordingly, the low transmission portions 80 can be formed in a state in which the vertical wrinkles are stretched to a large extent, and this state or a state close to this state can be maintained after manufacturing. However, the portions that are bonded as a result are discontinuous in the CD direction. Thus, deterioration of flexibility and deterioration of appearance can be prevented. In contrast, in the reference sample including the low transmission portions 80 that do not satisfy the above-described condition, many wrinkles along the MD direction are formed at intervals in the CD direction, and the appearance deteriorates.

The bonding pattern is not particularly limited, provided that, in the region between the convex portions 31 adjacent in the MD direction, a plurality of the low transmission portions 80 are arranged at intervals in the CD direction, and the interval portions in the CD direction are connected by the compressed portions 81. As illustrated in FIG. 11, it is preferable from the viewpoint of prevention of wrinkles that the low transmission portion 80 be formed at the center position in the CD direction corresponding to the center position in the CD direction of the adjacent convex portions 31 in the MD direction. However, as illustrated in FIG. 12, a pattern may preferably be such that the low transmission portion 80 is not formed at the center position in the CD direction, because flexibility can be enhanced. Additionally, in the former case, it is more preferable from the viewpoint of flexibility to make the area of the low transmission portion 80 at the center position in the CD direction smaller than an area of another low transmission portion 80.

As illustrated in FIG. 10 through FIG. 12, in addition to the configuration such that a plurality of sequences are formed at intervals in the MD direction in the regions between the adjacent convex portions 31 in the MD direction by obtaining sequences by arranging a plurality of low transmission portions 80 at intervals in the CD direction, a configuration may be adopted in which only one sequence is formed. The former is suitable for forming the concave portion 32 between the convex portions 31 to be wide, and the latter is suitable for forming the concave portion 32 between the convex portions 31 to be narrow. In the former configuration, in the interval portions of the low transmission portions 80 in the MD direction, the top sheet 22 and the intermediate sheet 25 are not welded, and the top sheet 22 and the intermediate sheet 25 may be compressed similar to the interval portions in the CD direction. However, if the top sheet 22 and the intermediate sheet 25 are not welded and the top sheet 22 is not compressed compared to the interval portions in the CD direction (which includes an uncompressed state in which the top sheet 22 is not compressed at all), more superior flexibility and appearance can be obtained.

The size of the low transmission portion 80 in each of the configurations illustrated FIG. 11 and FIG. 12 may be determined as appropriate. However, each low transmission portion 80 between the adjacent convex portions 31 in the MD direction may preferably be a point-like bonding part such that the length in the MD direction 80m is approximately from 0.1 to 0.4 times the center interval 31y in the MD direction of the CD direction sequences of the convex portions 31 adjacent in the MD direction (in a usual case, from 0.5 mm to 3 mm, for example), and the length in the CD direction 80c is approximately from 0.1 to 0.4 times the center interval 31x in the CD direction of the MD direction sequences of the convex portions 31 adjacent in the CD direction (in a usual case, from 0.5 mm to 3 mm, for example). Furthermore, the interval 80d in the CD direction between the adjacent low transmission portions 80 in the CD direction may preferably be approximately from 1 to 5 times the length 80c in the CD direction of the low transmission portion 80 (in a usual case, from 0.5 mm to 15 mm, for example), and a number of the low transmission portions 80 in the CD direction sequence may preferably be from 2 to 4.

In the configuration in which the convex portions 31 are arranged in a zigzag manner, the interval between the adjacent convex portions 31 in the CD direction is also the interval between the adjacent convex portion 31 in the MD direction. Thus, the low transmission portion 80 similar to that of the interval between the adjacent convex portions 31 in the MD direction may preferably be formed. However, the number and the arrangement may be changed.

The low transmission portions 80 in the configuration illustrated in FIG. 11 and FIG. 12 may be formed by a bonding pattern that is discontinuous in the width direction and the front-rear direction, and the interval in each direction can be suitably determined. For example, a CD direction bonding range A3 by each low transmission portion 80 between the adjacent convex portions 31 in the MD direction may preferably be approximately 0.3 to 1 times the center interval 31x in the CD direction of the MD direction sequences of convex portions 31 adjacent in the CD direction (in a usual case, from 1 mm to 10 mm, for example), and a MD direction bonding range A4 by each low transmission portion 80 between the adjacent convex portions 31 in the CD direction may preferably be approximately 0.3 to 1 times the center interval 31y in the MD direction of the CD direction sequences of convex portions 31 adjacent in the MD direction (in a usual case, from 1 mm to 10 mm, for example). If the CD direction bonding range A3 and the MD direction bonding range A4 are too wide, it is the same as the configuration in which the low transmission parts 80 continues in the CD direction and the MD direction, and the permeability and flexibility of the top sheet 22 may be lowered.

Figure 14:
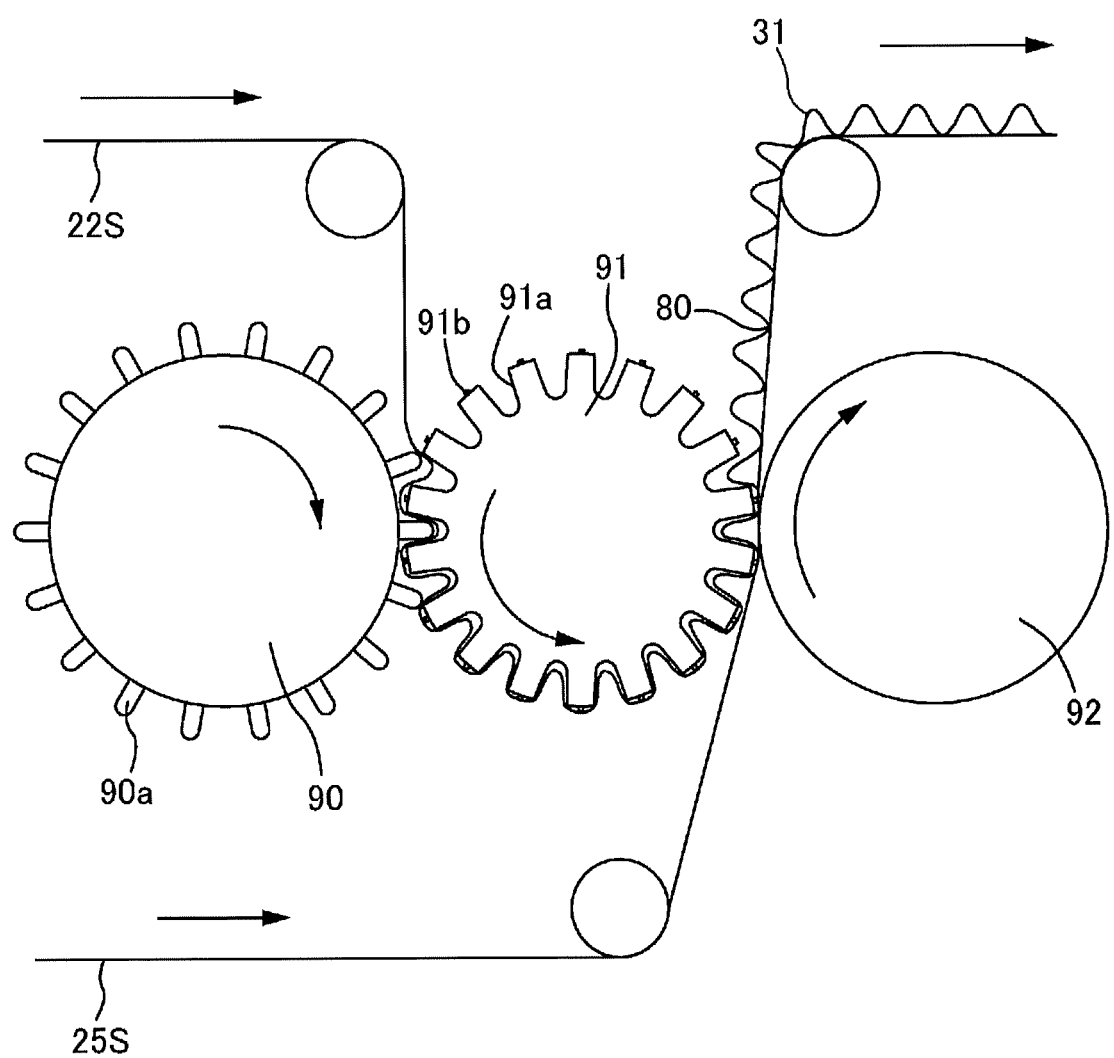
FIG. 14 is a diagram illustrating an example of assembly equipment of a top sheet and a second sheet.

FIG. 14 illustrating a processing facility for forming the above-described convex portions and the low transmission portions 80 and bonding the top sheet and the intermediate sheet. Namely, the facility includes a push-in roll 90; a concave roll 91 facing the push-in roll 90; and bonding roll 92 facing the concave roll 91.

Figure 17:
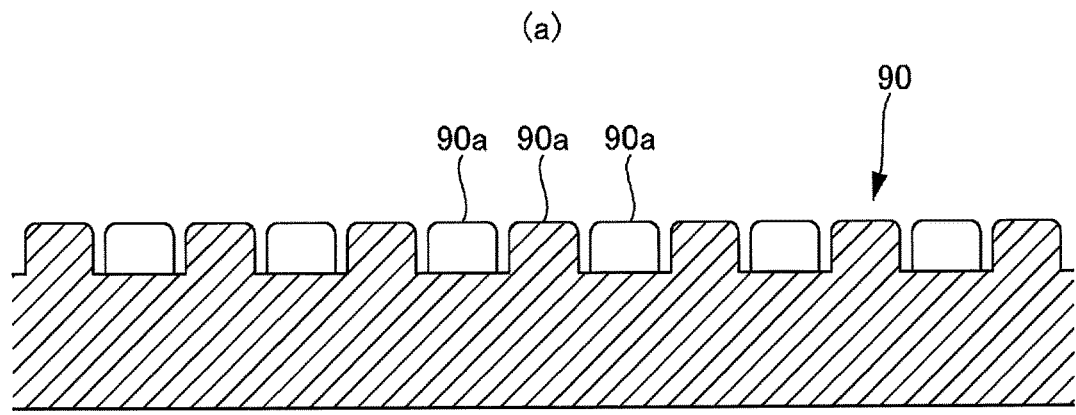
FIG. 17 is a diagram illustrating a cross-sectional view of main parts of a push-in roll (a) and an expanded plan view of a circumferential surface.
Figure 17:
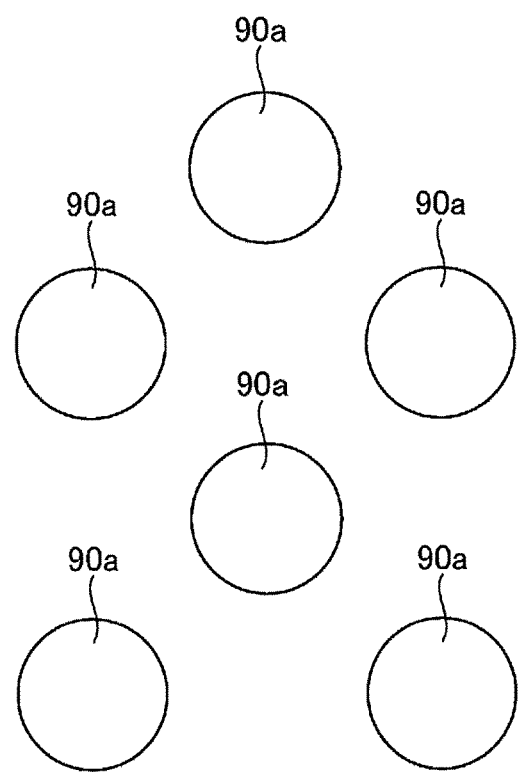

As illustrated in FIG. 17, in the push-in roll 90, a large number of push-in convex portions 90a are formed on the circumferential surface by the arrangement pattern of the convex portions 31. The shape of the convex portion of the push-in roll 90 may be suitably defined. However, the shape of the convex portion of the push-in roller 90 may be a truncated cone shape with a cross section (e.g., a circle, and ellipse, a regular polygon, etc.) that is adjusted to the shape of the convex portion 31.

Figure 18:
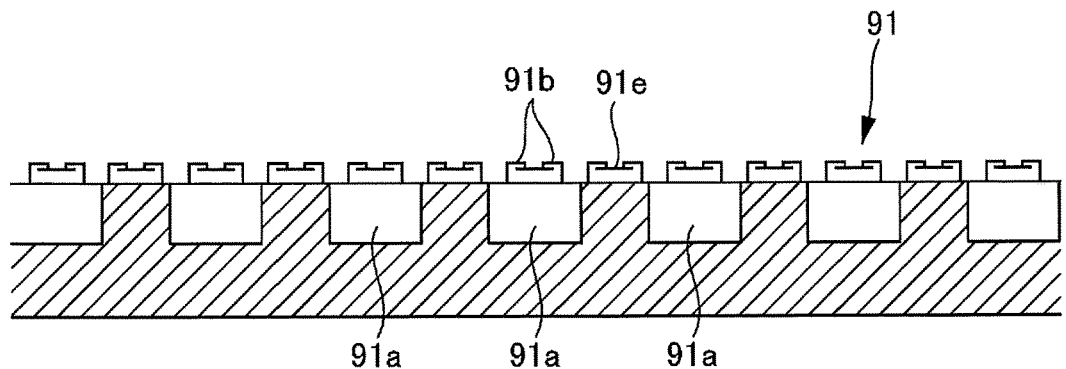
FIG. 18 is a diagram illustrating a cross-sectional view of main parts of a concave roll (a) and an expanded plan view of a circumferential surface.
Figure 18:
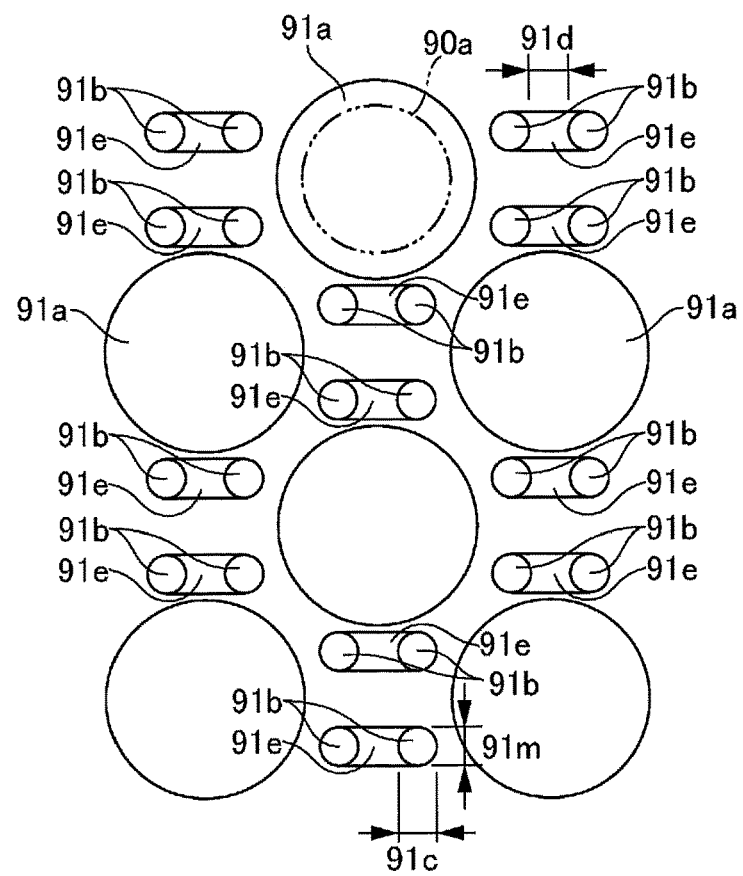

As illustrated in FIG. 18, in the concave roll 91, push-in concave portions 91a corresponding to the convex portions 90a of the push-in roll 90 are formed on the circumferential surface, and bonding convex portions 91b and compression convex portions 91e are formed between these push-in concave portions 91a. The bonding convex portion 91b is a portion for forming the low transmission portion 80 in the above-described bonding pattern. The compression convex portion 91e is a portion for compressing the nonwoven fabric 22S to be the top sheet 22 in the thickness direction without welding the top sheet 22 and a material 25S of the intermediate sheet in the interval portion in the CD direction of the low transmission portions 80. When the material 25S of the intermediate sheet is a material to be compressed in the thickness direction, such as the nonwoven fabric, the intermediate sheet 25 is also compressed at the same time by the compression convex portion 91e. More specifically, in the concave roll 91, in the region between the push-in concave portions 91a adjacent in the roll circumferential direction, a sequence obtained by arranging a plurality of bonding convex portions 91b at intervals in the roll axis direction is formed to cross the center position in the roll axis direction of the region, and the interval portions of the bonding convex portions 91b in the roll axis direction are the compression convex portions 91e. The portions other than the bonding convex portions 91b, the compression convex portions 91e, and the push-in concave portions 91a are portions that do not compress the material. However, these portions may be portions for performing compression at the same level as or lower than the compression by the compression convex portions 91e. The push-in concave portion 91a of the concave roll 91 may be an opening, which does not have a bottom surface, with a size that the push-in convex portion can enter, provided that the convex portion can be formed. The push-in concave portion 91a includes such an opening.

The size, the shape, and the arrangement of the push-in convex portion 90a in the push-in roll 90 correspond to the inner space size, the shape, and the arrangement of the convex portion 31 to be formed, and the size, the shape, and the arrangement of the push-in concave portion 91a in the concave roll 91 correspond to the outer size, the shape, and the arrangement of the convex portion 31 to be formed. Furthermore, the size, the shape, and the arrangement of the bonding convex portion 91b in the concave roll 91 correspond to the size, the shape, and the arrangement of the low transmission portion 80 to be formed, and the size, the shape, the arrangement of the compression convex portion 91e in the concave roll 91 correspond to the size, the shape, and the arrangement of the compressed portion 81, if the compressed portion 81 is to be formed. Accordingly, these size, shape, and arrangement may be changed similar to the size, shape, and arrangement of the convex portion 31, the low transmission portion, and the compressed portion, which are described in the section on the disposable diaper. For example, the length 91m in the MD direction, the length 91c in the CD direction, and the interval 91d in the CD direction of the bonding convex portion 91b in the configuration illustrated in (b) of FIG. 19 may be within the similar ranges as ranges of the length 80m in the MD direction, the length 80c in the CD direction, and the interval 80d in the CD direction of the low transmission portion 80 in the configuration illustrated in (b) of FIG. 12.

Figure 19:
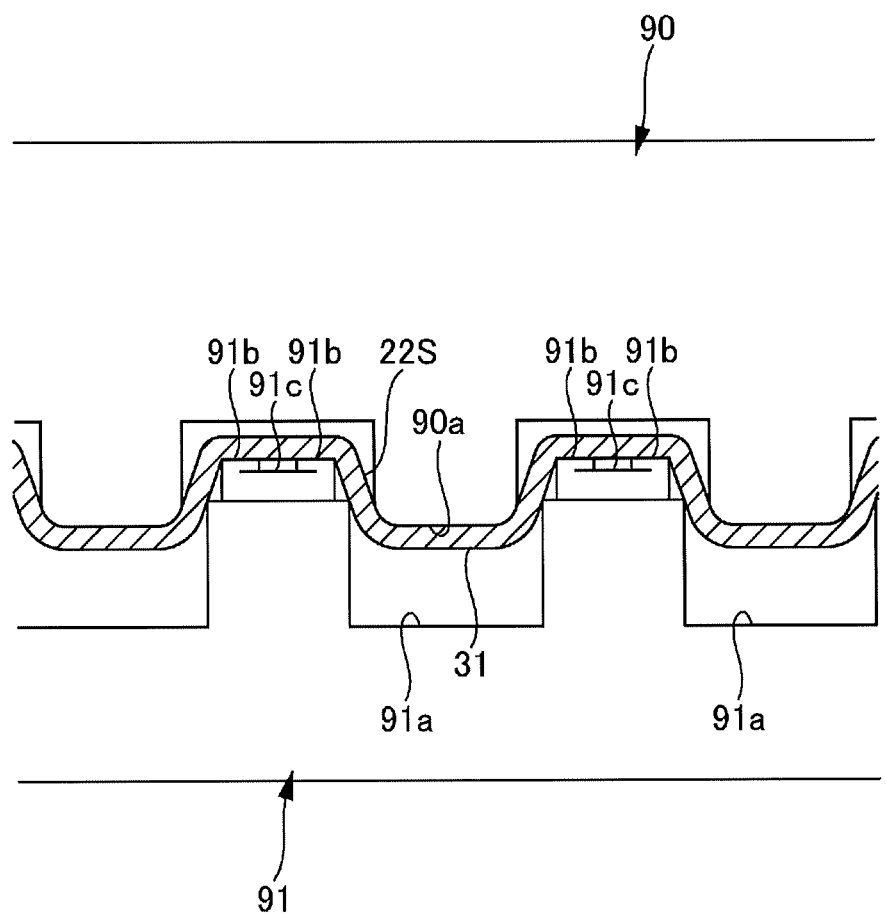
FIG. 19 is an enlarged cross-sectional view illustrating main parts in a convex part forming process by the push-in roll and the concave roll.

During processing, the convex portion 31 is formed by nipping the nonwoven fabric 22S between the push-in roll 90 and the concave roll 91, as illustrated in FIG. 19, while transferring the nonwoven fabric 22S to be the top sheet 22 by tension from the downstream side of the production line, and by performing the embossing process to push the convex portion of the push-in roll 90 into the push-in concave portion 91a of the concave roll 91.

Figure 20:
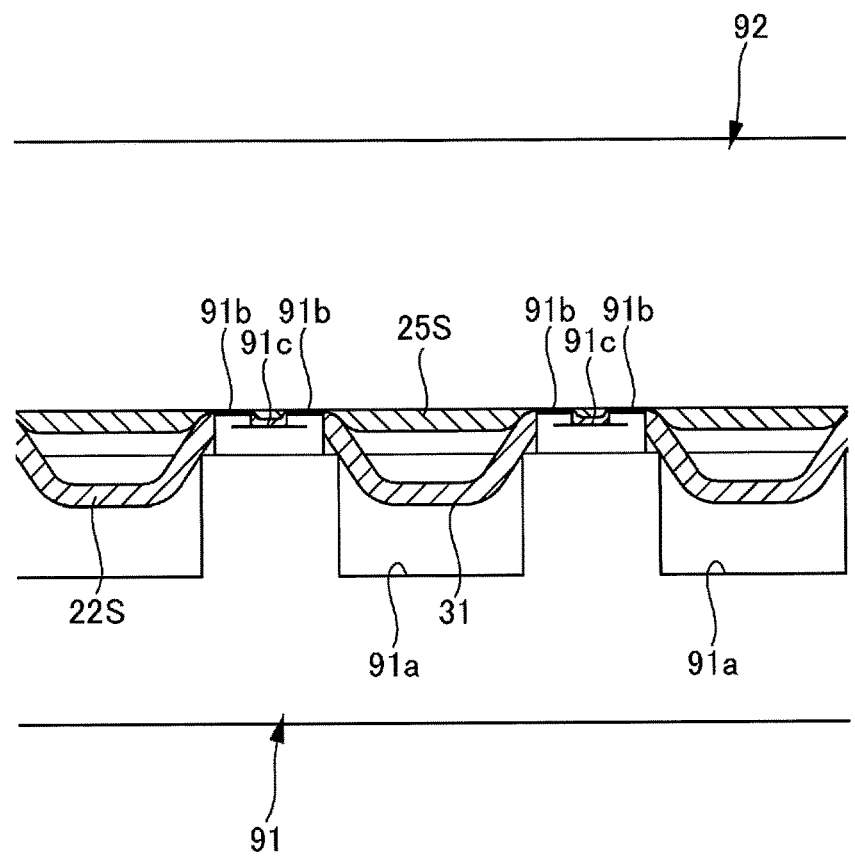
FIG. 20 is an enlarged cross-sectional view illustrating main parts in a bonding process by the concave roll and a bonding roll.
Figure 20:
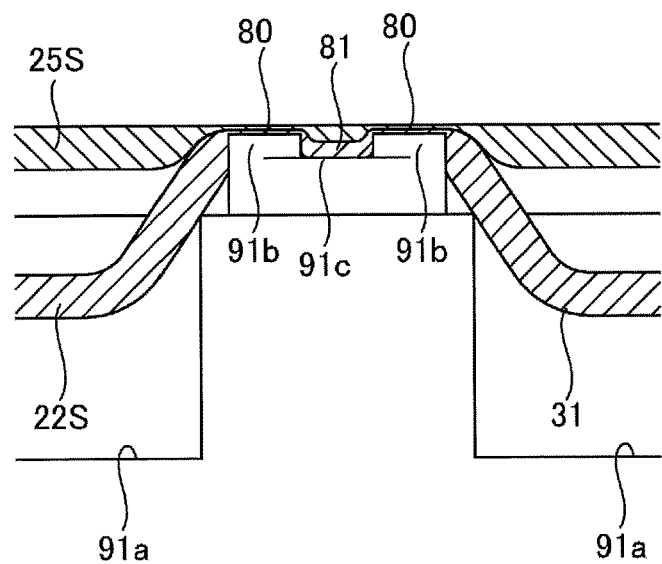
Figure 22:
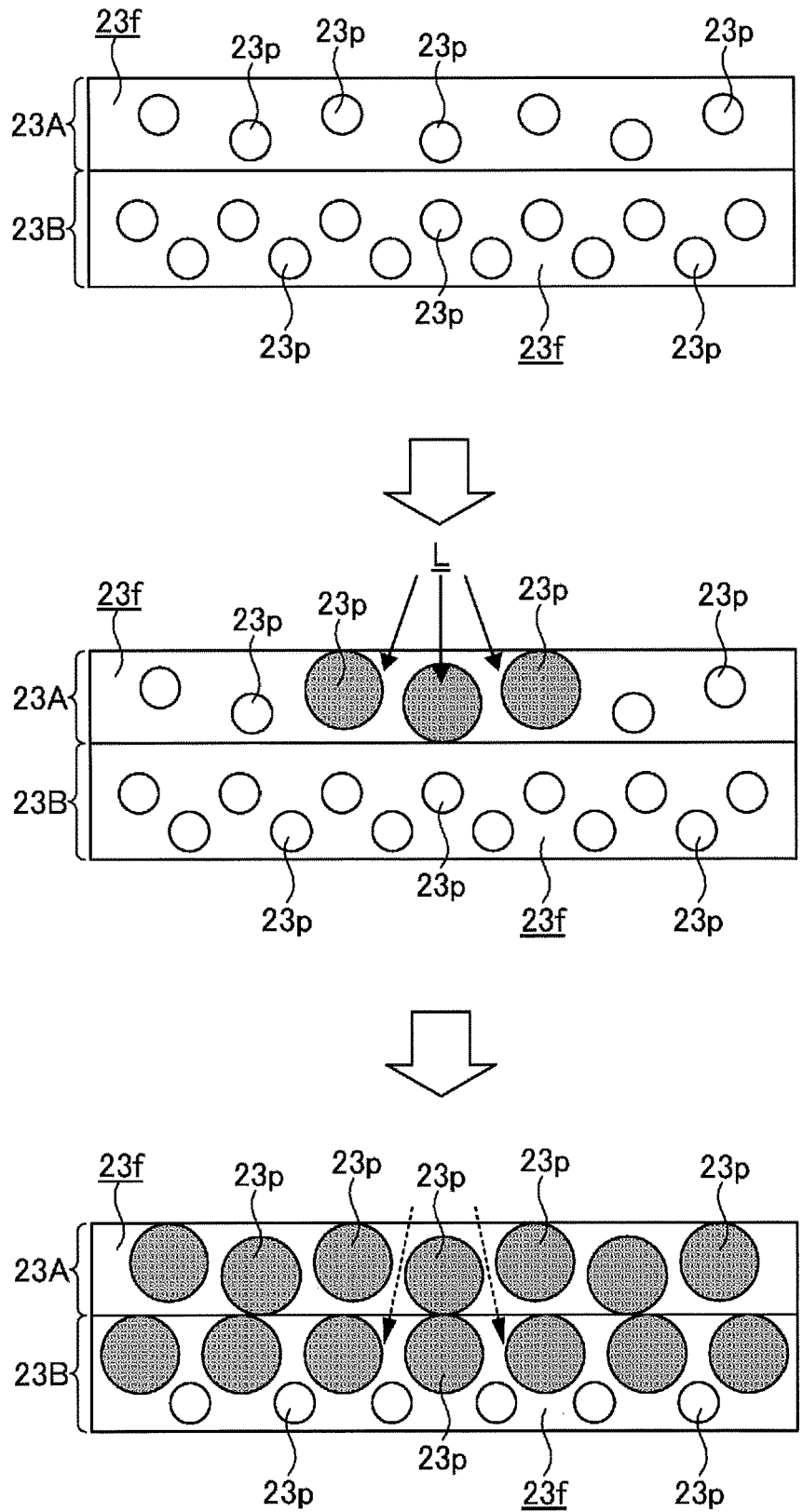
FIG. 22 is a cross-sectional view schematically illustrating an absorption mechanism of an absorbent.

Subsequently, in the process of guiding the nonwoven fabric 22S in which the convex portions 31 are formed as it is wrapped around the concave roll 91, the intermediate sheet material 25S is fed to the outside of the nonwoven fabric to be the top sheet 22 by tension from the downstream side of the production line. As illustrated in FIG. 20, the nonwoven fabric 22S to be the top sheet 22 and the intermediate sheet material 25S are nipped between the concave roll 91 and the bonding roll 92, and the nonwoven fabric 22S and the intermediate sheet material 25S are pressed and welded between the bonding convex portion 91b of the concave roll 91 and the peripheral surface of the bonding roll 92, while the nonwoven fabric 22S and the intermediate sheet material 25S are compressed between the compression convex portion 91e of the concave roll 91 and the peripheral surface of the bonding roll 92. Then, the low transmission portions 80 are formed, and an assembly of the top sheet 22 and the intermediate sheet 25 is manufactured. As result, even if a vertical wrinkle is formed between the adjacent convex portions 31 in the MD direction in the nonwoven fabric 22S to be the top sheet 22 at the time of forming the convex portions 31, since the pressure welding portion 80 and the compression portion 81 compressed without being welded are alternately continued in the CD direction so as to cross the vertical wrinkle during bonding to the intermediate sheet material 25S, the low transmission portion 80 can be formed in a state in which the vertical wrinkle is stretched to a large extent, and this state or a state close to this state can be maintained after manufacturing. However, the portions to be bonded as a result are discontinuous in the CD direction, so that deterioration of flexibility and deterioration of appearance can be prevented. As understood from this principle, not only the traces compressed by the compression convex portions 91e remain as the above-described compression portions 81 but also those having little or no trace of compression have the effect of preventing the vertical wrinkles.

As a pressure welding means, in addition to heat sealing for heating the roll and welding the material, an ultrasonic seal can be adopted, provided that the material can be compressed and welded in the thickness direction. A disposable diaper can be produced by assembling the processed assembly of the top sheet 22 and the intermediate sheet 25 to an absorbent, etc., by a known method.

As in the embodiment illustrated in FIG. 14, wrinkles tend to remain more easily in the processing method in which the material is bonded to the material of the intermediate sheet 25 in a state where the wrinkles are not absorbed, soon after the formation of the convex portions 31. Accordingly, it is preferable to adopt the above-described bonding pattern. If the low transmission portions 80 are formed after forming the convex portions 31 by embossing, it is not necessary to use the processing facility with the three rolls. In the depicted example, the nonwoven fabric to be the top sheet 22 is directly fed to the position at which the push-in roll 90 engages the concave roll 91. However, the nonwoven fabric to be the top sheet 22 may be fed so as to be wound only around the push-in roll 90 from the tangential direction of the circumferential surface of the push-in roll 90, and the nonwoven fabric may be guided so as to be transferred to the circumferential surface of the concave roll 91 after nipping the nonwoven fabric with the concave roll 91.

<Description of the Language in the Specification>

If the following terms are used in the specification, unless particularly described in the specification, the terms have the following meanings.

The "front-rear (vertical) direction" means the direction connecting the ventral (anterior) and dorsal (back), a "width direction" means a direction (lateral direction) perpendicular to the front-rear direction.

The "MD direction (machine die Les transfection or line flow direction)" and "CD direction (lateral direction perpendicular to the MD direction)" in the production process, means "MD direction" and the "CD direction" of the processing equipment of the convex portion 31 and, one of them becomes the front-rear direction and the other becomes the width direction. Further, the MD direction in the product is the direction of the fiber orientation of the nonwoven fabric. The fiber orientation is the direction along the fibers of the nonwoven fabric, for example, measuring method and in accordance to the fiber orientation test according to the zero distance tensile strength of TAPPI Standard Method T481, fibers from tensile strength ratio in the longitudinal direction and the width direction it can be determined by a simple measurement method for determining the orientation direction. In the depicted embodiment, the front-rear direction is the MD direction, and the width direction is the CD direction, similar to many many disposable diaper products.

The "developed state" means a state in which it is developed to be flat without shrinkage and loosening.

The "elongation rate" means a value when the natural length is 100%.

The "total basis weight" is measured as follows.

After preliminary drying a sample or a test piece, it is left in a test chamber or device in the standard state (the test location is such that the temperature is 20±5° C. and relative humidity is less than or equal to 65%), and it becomes constant weight. The preliminary drying refers to making the sample or the test piece to be constant weight in an environment in which the relative humidity is from 10% to 25%, and the temperature does not exceed 50° C. Note that the fibers with an official moisture regain is 0.0%, and preliminary drying may not be performed. Using a rice plate (200 mm×250 mm, ±2 mm), a sample with a size of 200 mm×250 mm (±2 mm) is cut from the test piece in the constant weight condition. The total basis weight is obtained by measuring the weight of the sample, and by calculating the weight per 1 square meter by multiplying by 20.

The "thickness" of the top sheet 22 and the intermediate sheet 25 illustrated in FIGS. 10 to 20 means the apparent thickness, which is measured by the method described on paragraph [0017] of Japanese Patent No. 3611838. That is, in the measurement, while bonding the top sheet 22 and the intermediate sheet 25, a measurement piece of vertical 30 mm×horizontal 30 mm is cut out. Then, a cutting surface is formed with a line that is substantially parallel to the vertical direction [the fiber orientation direction (flow direction during producing nonwoven fabrics) of the nonwoven fabric (fiber aggregate) forming the top sheet 22] and that passes through the low transmission portion 80. The enlarged photograph of the cutting surface is captured using Keyence digital microscope VHX-1000, etc., and the maximum apparent thickness of the top sheet 22 is obtained based on this enlarged photograph, which is defined to be the thickness of the top sheet 22. In the measurement portion of the maximum thickness of the top sheet 22, the apparent thickness of the intermediate sheet 25 is measured, which is determined to be the thickness of the intermediate sheet 25. Further, as the size in the direction of the cross section, such as the thickness of another portion (the thickness of the low transmission portion 80, the thickness, etc., of the compressed portion 81) and the height 31z, etc., of the convex portion 31, the height of the protrusion from the bottom to the top of the convex portion is measured, similar to the measurement of the "thickness" of the top sheet and the intermediate sheet.

The "thickness" of the absorbent is measured by holding the sample and the thickness measuring instrument horizontally, and by using the thickness measuring instrument Ozaki Manufacturing Co., Ltd. (Peacock, dial thickness gauge large type, model J-B (measurement range 0-35 mm) or Type K-4 (measuring range 0-50 mm)) used.

The "thickness" other than the above-described thickness is automatically measured using the automatic thickness measuring instrument (KES-G5 Handy Compression measurement program), under the conditions of load: 10 gf/cm$^2$, and the pressure area: 2 cm$^2$.

The water absorption amount is measured by JIS K7223-1996 "water absorption amount test method of superabsorbent resin."

The water absorption rate is defined to be the "time to end point" when JIS K7224-1996 "water absorption rate test method for superabsorbent resin" is performed using 2 g of superabsorbent polymer and 50 g of physiological saline superabsorbent polymer.

If there is no description of the environmental conditions of testing and measurement, the test and measurement are assumed to be performed in the laboratory or in the device in the standard conditions (the test location is such that the temperature is 20±5° C. and the relative humidity is less than or equal to 65%).

Unless otherwise specified, the size of each part is the size in the developed state, and not the size in the state the natural length.

INDUSTRIAL APPLICABILITY

The present invention can be used for a pad type disposable diaper, such as that of the above-described example.

DESCRIPTION OF REFERENCE SYMBOLS

B2 rear portion, C2 crotch portion, F2 front portion, 11 region including low transmission portions, liquid impermeable sheet, 22 top sheet, 23A, 23B absorbents, 24 three-dimensional gather, 24s gather sheet, 25 intermediate sheet, 26 packaging sheet, 27 outer covering sheet, 30 depressed portion, 31 convex portion, 40 slit, 41 another slit, 200 pad type disposable diaper, 80 low transmission portion, 23A upper layer absorbent, 23B lower layer absorbent

The invention claimed is:

1. A pad type disposable diaper comprising:
   a crotch portion;
   a front portion that extends toward a front side of the crotch portion;
   a rear portion that extends toward a rear side of the crotch portion;
   an absorbent provided in a front-rear direction range including the crotch portion; and
   a top sheet covering a surface side of the absorbent,
   wherein the absorbent is formed of a lower layer absorbent and an upper layer absorbent formed on a surface side of the lower layer absorbent,
   wherein a pair of left and right slits that pass through only the upper layer absorbent or the upper layer absorbent and the lower layer absorbent in a thickness direction is extended in a front-rear direction region including the crotch portion,
   wherein each of the pair of left and right slits has a predetermined width, and the left slit and the right slit are spaced apart in a width direction,
   wherein the top sheet includes a depressed portion that falls into the slits,
   wherein, in at least a region located between the slits in the top sheet, a large number of convex portions protruding toward the surface side is arranged in a zigzag manner while being spaced apart by an interval, and the interval between the adjacent convex portions in the width direction is shorter than each of sizes in the width direction of the convex portions located at the front side and at a rear side of a part of the interval, and
   wherein a weight ratio of superabsorbent polymer particles with respect to pulp fibers in the upper layer absorbent is greater than a weight ratio of the superabsorbent polymer particles with respect to the pulp fibers in the lower layer absorbent.

2. The pad type disposable diaper according to claim 1, wherein a front end of the slit is separated rearward from a front end of the absorbent, and wherein the region in which the convex portions are arranged extends to the front side of the slit.

3. The pad type disposable diaper according to claim 1, wherein a size in the front-rear direction of the convex portion is from 1.1 mm to 12.0 mm, a size in the width direction of the convex portion is from 2.3 mm to 9.2 mm, and the size in the front-rear direction of the convex portion is 0.5 to 1.3 times the size in the width direction of the convex portion, wherein, in a sequence of the convex portions arranged in the front-rear direction, a distance between centers of the convex portions in the front-rear direction is preferably from 1.9 mm to 20.9 mm, wherein, in a sequence of the convex portions arranged in the width direction, a distance between the centers of the convex portions in the width direction is preferably from 4.0 mm to 16.0 mm, and wherein the distance between the centers of the convex portions in the front-rear direction in the sequence of the convex portions arranged in the front-rear direction is 0.5 to 1.3 times the distance between the centers of the convex portions in the width direction in the sequence of the convex portions arranged in the width direction.

4. The pad type disposable diaper according to claim 3, wherein, while the fibers are mutually welded in the low transmission portion, the low transmission portion is welded to a component at a reverse side.

5. The pad type disposable diaper according to claim 1, wherein the top sheet is formed of thermoplastic nonwoven fabric, and wherein a low transmission portion, in which fibers are mutually welded in a state in which the fibers are compressed in a thickness direction, is provided between the convex portions in the top sheet.

6. The pad type disposable diaper according to claim 5, wherein a plurality of low transmission portions is formed while spaced apart by a gap.

7. The pad type disposable diaper according to claim 1, wherein the convex portions are also formed in the depressed portion.

* * * * *